United States Patent [19]

Schloemer

[11] Patent Number: 4,605,758

[45] Date of Patent: Aug. 12, 1986

[54] PREPARATION OF α-ARYLALKANOIC ACIDS

[75] Inventor: George C. Schloemer, Lyons, Colo.

[73] Assignee: Syntex Pharmaceuticals International Ltd., Hamilton, Bermuda

[21] Appl. No.: 602,834

[22] Filed: Apr. 23, 1984

Related U.S. Application Data

[63] Continuation of Ser. No. 329,672, Dec. 11, 1981, abandoned.

[51] Int. Cl.$^4$ .............................................. C07C 51/16
[52] U.S. Cl. ................................... 562/418; 549/369; 549/374; 549/420; 549/453; 549/455; 556/118; 556/436; 560/8; 560/20; 560/21; 560/51; 560/52; 560/55; 560/56; 560/57; 560/100; 560/102; 560/105; 562/405; 562/434; 562/419; 562/435; 562/459; 562/462; 562/465; 562/466; 562/460; 568/323; 568/328; 562/490; 568/335; 568/336; 562/492; 568/337; 568/425; 562/496; 568/426; 568/592; 568/309; 558/51; 568/319
[58] Field of Search .............. 568/424, 437, 323, 309, 568/319; 562/418, 419, 490, 496

[56] References Cited

U.S. PATENT DOCUMENTS

| | | | |
|---|---|---|---|
| 2,397,412 | 3/1946 | Emerson | 568/437 |
| 2,444,400 | 6/1948 | Emerson | 568/426 |
| 2,824,139 | 2/1978 | Barnhart | 568/323 |
| 2,873,275 | 2/1959 | Ramsden | 568/323 |

FOREIGN PATENT DOCUMENTS 55-130934  10/1980  Japan ................... 568/323

OTHER PUBLICATIONS

Kharasch, "Grignard Reactions of Nonmetallic Substances," pp. 709–766, 846–851 and 870–879 (1954).
Cason, J. Am. Chem. Soc., 68, p. 2076 (1946).
Milsow, J. Am. Chem. Soc., 75, pp. 2318–2322 (1953).
Seebach, Angew. Chem. Internat. Ed., 7, pp. 619–621 (1968).

*Primary Examiner*—Michael L. Shippen
*Attorney, Agent, or Firm*—John A. Dhuey

[57] ABSTRACT

Pharmaceutically useful optically active α-arylalkanoic acids or esters, ortho esters, or amides thereof are stereoselectively prepared by contacting an aryl magnesium Grignard reagent with an optically active α-substituted acyl halide to form the optically active aryl α-substituted alkyl ketone, which is ketalized and rearranged to the desired optically active α-arylalkanoic acid or the corresponding ester, ortho ester or amide. In an alternate embodiment, the aryl α-substituted alkyl ketone is reduced to the corresponding alkanol, which is rearranged to the α-arylalkanal. The alkanal so produced is converted to the desired optically active α-arylalkanoic acid by conventional methods.

24 Claims, No Drawings

PREPARATION OF α-ARYLALKANOIC ACIDS

This is a continuation of application Ser. No. 329,672, filed Dec. 11, 1981, abandoned.

BACKGROUND OF THE INVENTION

1. Field of the Invention

The present invention relates to a process for preparing pharmaceutically useful α-arylalkanoic acids. In particular, it relates to a stereoselective process for producing optically active α-arylalkanoic acids which are substantially optically pure.

2. State of the Art

Numerous α-arylalkanoic acids (i.e. 2-arylalkanoic acids) have been described, developed and found to be useful as pharmaceutical agents exhibiting anti-inflammatory, analgesic and anti-pyretic activity. For example, U.S. Pat. No. 3,385,386, describes certain 2-phenylpropionic acids useful for their anti-inflammatory activity. Particularly noteworthy of the compounds described therein is 2-(4-isobutylphenyl)propionic acid, known generically as ibuprofen. U.S. Pat. No. 3,600,437 describes 2-(3-phenoxyphenyl)- and 2-(3-phenylthiophenyl)alkanoic acids among other related compounds. Particularly noteworthy therein is the compound 2-(3-phenoxyphenyl)propionic acid, which is known generically as fenoprofen. U.S. Pat. No. 3,624,142 describes (fluoro-substituted biphenyl)alkanoic acids, among which is 2-(4'-fluoro-4-biphenylyl)propionic acid. U.S. Pat. No. 3,755,427 describes additional fluoro-substituted biphenylpropionic acids, among which is 2-(2-fluoro-4-biphenylyl)propionic acid, known as flurbiprofen. U.S. Pat. No. 3,904,682 describes the compound 2-(6-methoxy-2-naphthyl)propionic acid, the d-isomer of which is known generically as naproxen and is a potent anti-inflammatory compound. Related compounds are described in Belgian Pat. No. 747,812. U.S. Pat. No. 3,912,748 describes 5- and 6-benzoxyazoylalkanoic acids possessing anti-inflammatory, anti-pyrretic and analgesic activity. Notable among those compounds is 2-(4-chlorophenyl-5-benzoxazoyl)propionic acid, known generically as benoxaprofen. Thus, it can be seen that a tremendous variety of useful α-arylalkanoic acids are known.

Other known, useful α-arylalkanoic acids are exemplified by 6-chloro-α-methyl-9H-carbazole-2-acetic acid (carprofen), α-methyl-9H-fluorene-2-acetic acid (cicloprofen), 3-chloro-α-methyl-4-(2-thienylcarbonyl)-benzene acetic acid (cliprofen), α-methyl-3-phenyl-7-benzofuranacetic acid (furaprofen), 4-(1,3-dihydro-1-oxo-2H-isoindol-2-yl)benzene acetic acid (indoprofen), 3-benzoyl-α-methylbenzene acetic acid (ketoprofen), 3-chloro-4-(2,5-dihydro-1H-pyrrol-1-yl)benzeneacetic acid (pirprofen), α-methyl-4-(2-thienylcarbonyl)benzeneacetic acid (suprofen) and compounds related thereto. Additionally, certain pyrethroid-type insecticides utilize optically active α-arylalkanoic acids, e.g. α-(4-chlorophenyl)isovaleric acid, α-(4-difluoromethoxyphenyl)isovaleric acid and the like, in their formulations.

Numerous processes for the manufacture of such α-arylalkanoic acids have also been described. Such processes have been described in the aforementioned patents, in other patents and in the non-patent literature as well. For example, U.S. Pat. No. 4,135,051 describes a process for preparing the ester precursors of many of the useful arylalkanoic acids utilizing trivalent thallium salts as reactants. Such a process suffers from the disadvantage that the thallium salts employed are toxic chemicals which must be removed from the final product. U.S. Pat. No. 3,975,431 describes the preparation of α-arylalkanoic acids from glycidonitriles through enol acylates. U.S. Pat. Nos. 3,658,863; 3,663,584; 3,658,858; 3,694,476; and 3,959,364 describe various coupling methods for preparing arylalkanoic acids. More recently, U.K. Patent publication No. 2,042,543 published Sept. 24, 1980, (corresponding to application Ser. No. 8005752, filed Feb. 20, 1980) describes a process for preparing the ester precursor of arylalkanoic acids from α-haloalkyl aryl ketones using a metal catalyst for catalytically inducing rearrangement in an acidic, alcoholic medium, the catalyst being silver (I) salts of organic and/or inorganic anions. The high costs associated with utilizing metal catalysts, particularly silver, in a large scale process is an inherent disadvantage to such a process. European Patent Application No. 81200210.3, filed Feb. 23, 1981 (Publication No. 0034871, published Sept. 2, 1981) describes a process for preparing esters of α-arylalkanoic acids via rearrangement of α-haloketals in the presence of a Lewis acid (including, for example, copper and zinc salts and the like). Additionally, a recent article in Tetrahedron Letters, Vol. 22, No. 43, pp 4305–4308 (1981) describes a process for producing α-arylalkanoic acids by 1,2-rearrangement of the aryl group via hydrolysis of α-sulfonyloxy acetals.

While the aforesaid processes are useful in many respects, there remains a need for a simple, economical process for producing α-arylalkanoic acids of the types described. Furthermore, in view of the optically active nature of numerous of the α-arylalkanoic acids, it is advantageous to have a stereoselective process for producing the desired optically active isomer of the α-arylalkanoic acids which displays all or the major portion of the pharmaceutical activity. For example, the isomer d 2-(6-methoxy-2-naphthyl)propionic acid is more pharmaceutically active than the corresponding l-isomer, and, accordingly, it is desireable to have a stereoselective process for producing the d-isomer directly. Such a process obviates the necessity of subsequently resolving the d- and l-isomers. The elimination of the resolution steps results in substantial economic savings, both in material cost and manufacturing labor and plant usage. These savings are particularly significant with regard to those compounds which are approved for pharmaceutical use as a substantially pure, optically active isomer [e.g. d 2-(6-methoxy-2-naphthyl)propionic acid].

SUMMARY OF THE INVENTION

The present invention is directed to a process for producing an optically active α-arylalkanoic acid or an ester, ortho ester or amide thereof comprising contacting an organometallic compound, e.g. an aryl magnesium Grignard reagent, with an acyl halide, an acyl amine or an acid anhydride, the acyl halide, acyl amine or acid anhydride being substituted with a leaving group or a group which can be converted into a leaving group. In one aspect, the present invention comprises contacting an aryl organometallic halide with an optically active α-substituted acyl halide, acyl amine or acid anhydride to form the corresponding optically active aryl alkyl ketone, wherein the α-substituent is a leaving group. The ketone group then is ketalized and the substrate formed is rearranged and hydrolyzed to the desired optically active α-arylalkanoic acid. During the rearrangement step of the process, the leaving group disassociates from the substrate and the aryl group migrates to the α-position to afford the rearranged, optically active α-arylalkanoic acid. That aspect of the invention is exemplified by the contacting of an aryl magnesium Grignard reagent with an optically active α-sulfonyloxy acyl halide to form the corresponding aryl α-sulfonyloxyalkyl ketone.

The optically active ketones and ketals so produced represent an additional aspect of the present invention. By alternative processes, those ketones can be converted into the desired optically active α-arylalkanoic acids listed previously.

In one embodiment of the invention, the optically active ketones produced are subjected to ketalization under conditions which are amenable to retaining the desired stereochemical configuration at the asymmetric carbon atom of the ketone. For example, ketalization of the ketone with an ortho ester under conditions of acid catalysis affords the desired optically active ketal with retention of the desired configuration at the asymmetric carbon atom. Subsequent solvolytic rearrangement of the ketal yields the desired α-arylalkanoic acid, or the ester, ortho ester or amide thereof. By appropriate choice of the optical configuration of the substituted acyl halide, or the acyl amine or acid anhydride, in view of the single inversion during the rearrangement step, it is possible to produce a desired optically active α-acylalkanoic acid.

The optically active ketone described above can also be subjected to a ketalization process which results in inversion of configuration at the asymmetric carbon atom of the ketone. For example, treatment of the ketone with alkali metal alkoxides or aryloxides typically affords a ketal in which the absolute configuration at the asymmetric carbon atom has inverted. Subsequent solvolytic rearrangement results in an additional inversion at the asymmetric carbon atom to produce the other optically active isomer of the desired α-arylalkanoic acid, or an ester, ortho ester or amide thereof, assuming that the starting ketone in both instances is the same. However, by appropriately choosing the absolute configuration of the starting acyl halide, acyl amine or acid anhydride, it is possible to cause the reaction sequence to yield the desired α-arylalkanoic acid in each instance.

In a further embodiment, the optically active ketone described above can be reduced to the corresponding arylalkanol, and then subjected to solvolytic rearrangement to afford the rearranged aldehyde. The aldehyde then can be converted to the desired optically active α-arylalkanoic acid by oxidation methods which are conventional in the art.

In one aspect, the present invention is directed to a process for producing a compound of the formula:

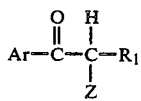

which comprises contacting an organometallic compound of the formula:

ArMX, (Ar)$_2$M or ArM' with an acyl halide, an acyl amine or an acid anhydride of the formula:

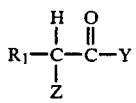

wherein Ar is aryl, M is cadmium, copper(II), manganese, magnesium or zinc, M' is copper(I) or lithium, R$_1$ is alkyl or cycloalkyl, X is halogen, Y is halogen or a group of the formula:

wherein R' and R" are alkyl or aryl or when taken together with N form a heterocyclic moiety which optionally can contain other hetero atoms on the ring, or acyloxy, and Z is a leaving group or a group that can be converted to a leaving group. Within that aspect of the invention, the presently preferred embodiment is characterized by use of an organometallic compound of the formula ArMX, preferably a magnesium Grignard reagent, and an acyl halide wherein Z is halogen or a group of the formula:

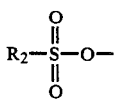

wherein R$_2$ is alkyl, cycloalkyl, alkenyl, alkynyl, aryl or arylalkyl. When Ar is 6-methoxy-2-naphthyl, the utilization of an optically active substituted acyl halide is desirable.

In another aspect, the present invention is directed to a process for producing a single stereoisomer of a compound of the formula:

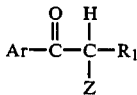

in the substantial absence of any other stereoisomer of the compound, which comprises contacting an organometallic compound of the formula:

ArMX, (Ar)$_2$M or ArM' with an optically active acyl halide, an acyl amine or an acid anhydride of the formula:

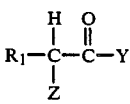

wherein Ar, M, M', R$_1$, X, Y and Z are as defined above.

In still another aspect, the invention is directed to a process for producing a single stereoisomer of a ketal of a compound of the formula:

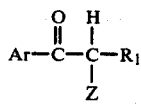

in the substantial absence of any other stereoisomer of the ketal, the single stereoisomer of the ketal having a preselected absolute configuration, which comprises contacting a stereoisomer of the compound having the preselected absolute configuration in the substantial absence of any other stereoisomer of the compound with a ketalizing agent effective to maintain the preselected absolute configuration, wherein Ar, $R_1$ and Z are as defined above. That aspect of the invention is particularly characterized by conducting the ketalization with a trialkyl ortho ester such as trimethyl orthoformate or a polyhydric alcohol such as ethylene glycol in the presence of an acid catalyst.

In another aspect, the invention is directed to a process for producing an α-arylalkanoic acid of the formula:

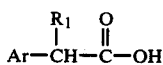

or an ester, ortho ester or amide thereof which comprises:

contacting a compound of the formula:

ArMX, (Ar)$_2$M or ArM' with an acyl halide, an acyl amine or an acid anhydride of the formula:

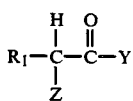

to form a ketone of the formula:

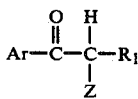

wherein Ar, M, M', $R_1$, X, Y and Z are as defined above;

contacting the ketone with a ketalizing agent effective to form a first ketal of the formula:

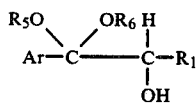

wherein $R_5$ and $R_6$ are alkyl, aryl or aralkyl, optionally the same or different, or, when taken together, alkylene having 2–8 carbon atoms;

regenerating a leaving group at the α-position of the first ketal to form a second ketal of the formula:

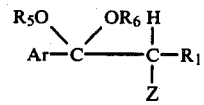

rearranging the second ketal to the α-arylalkanoic acid, or an ester, ortho ester or amide thereof; and optionally hydrolyzing any ester, ortho ester or amide formed to the corresponding α-arylalkanoic acid.

In yet another aspect, the invention is directed to a process for producing a stereoisomer of an α-arylalkanoic acid of the formula

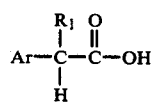

or an ester, ortho ester or amide thereof in the substantial absence of any other stereoisomer of the α-arylalkanoic acid, ester, ortho ester or amide thereof which comprises:

contacting a compound of formula:

ArMX, (Ar)$_2$M or ArM' with an optically active acyl halide, acyl amine or acid anhydride of the formula:

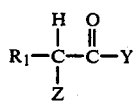

to form a single stereoisomer of an aryl alkyl ketone of the formula:

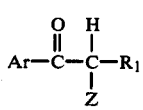

in the substantial absence of any other stereoisomer of the aryl alkyl ketone, wherein Ar, M, M', $R_1$, X, Y and Z are as defined above;

ketalizing the single stereoisomer of the aryl alkyl ketone to form a single stereoisomer of an aryl alkyl ketal thereof in the substantial absence of any other stereoisomer of the aryl alkyl ketal;

rearranging the single stereoisomer of the aryl alkyl ketal to form a single stereoisomer of the α-arylalkanoic acid or of an ester, ortho ester or amide thereof, in the substantial absence of any other stereoisomer of the α-arylalkanoic acid, ester, ortho ester or amide thereof; and optionally hydrolyzing any ester, ortho ester or amide formed to the corresponding α-arylalkanoic acid.

Presently preferred leaving groups exemplified by Z are halogen or the group:

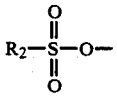

wherein $R_2$ is alkyl, cycloalkyl, alkenyl, alkynyl, aryl or arylalkyl.

In yet another aspect, the invention is directed to a process for producing a stereoisomer of an α-arylalkanoic acid of the formula:

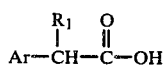

or an ester, ortho ester or amide thereof in the substantial absence of any other stereoisomer of the α-arylalkanoic acid, or the ester, ortho ester or amide thereof which comprises:

contacting a compound of the formula:

ArMX, (Ar)₂M or ArM' with an optically active acyl halide, acyl amine or acid anhydride of the formula:

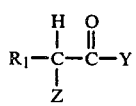

to form an optically active ketone of the formula:

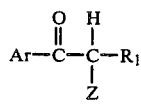

wherein Ar, M, M', R₁, X, Y and Z are as defined above;

contacting the ketone with a ketalizing agent effective to form an optically active first ketal of the formula:

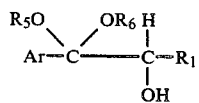

wherein R₅ and R₆ are alkyl, aryl or aralkyl, optionally the same or different, or, when taken together, alkylene having 2–8 carbon atoms;

regenerating a leaving group at the α-position of the first ketal to form an optically active second ketal of the formula:

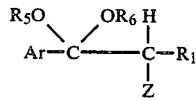

rearranging the optically active second ketal to the stereoisomer of the α-arylalkanoic acid, or an ester, ortho ester or amide thereof; and optionally hydrolyzing any ester, ortho ester or amide formed to the corresponding α-arylalkanoic acid.

In still another aspect, the present invention is directed to optically active ketones having an absolute (S)-configuration of the formula:

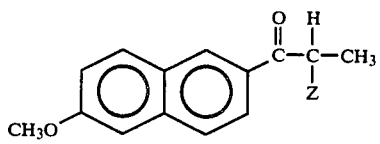

wherein Z is halogen, hydroxy, acetoxy, benzoyloxy, dihydropyranyloxy, trialkylsiloxy or the group:

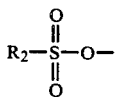

wherein R₂ is alkyl, cycloalkyl, alkenyl, alkynyl, aryl or arylalkyl.

In still another aspect, the invention is directed to optically active ketals having an absolute (S)-configuration of the formula:

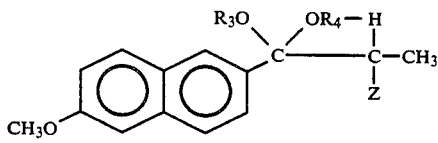

wherein R₃ and R₄ are alkyl, optionally the same or different, or, when taken together, are alkylene having 2–8 carbon atoms, and Z is halogen, hydroxy, acetoxy, benzoyloxy, dihydropyranyloxy, trialkylsiloxy or the group

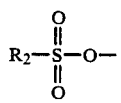

wherein R₂ is alkyl, cycloalkyl, alkenyl, alkynyl, aryl or arylalkyl, with the provision that when R₃ and R₄ are methyl, R₂ is not d-10-camphoryl.

DETAILED DESCRIPTION OF THE INVENTION

The process of this invention utilizes as starting materials organometallic compounds of the formula:

ArMX, (Ar)₂M or ArM'  (I)

wherein Ar is an aryl moiety, M is cadmium, copper(II), manganese, magnesium or zinc, M' is copper (I) or lithium, and X is a halogen atom. Other starting materials useful in the present invention are substituted acyl halides, acyl amines or acid anhydrides, which may be racemic compounds or optically active compounds, of the general formula:

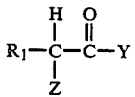  (II)

wherein R₁ is alkyl or cycloalkyl, Y is halogen, a group of the formula:

wherein R' and R" are alkyl or aryl or when taken together with N form a heterocyclic moiety which optionally can contain other hetero atoms in the ring, or acyloxy, and Z is a leaving group or a group that can be converted to a leaving group. Presently preferred leaving groups are those in which Z is halogen or a group of the formula:

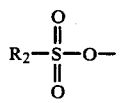

wherein $R_2$ is alkyl, cycloalkyl, alkenyl, alkynyl, aryl or aralkyl.

For the purposes of this invention, alkyl includes straight or branched chain aliphatic groups having 1-18 carbon atoms as exemplified by methyl, ethyl, propyl, isopropyl, n-butyl, sec-butyl, tert-butyl, amyl, hexyl, heptyl, octyl, decyl, dodecyl and octadecyl. Those alkyl groups having 1-8 carbon atoms, and especially those having 1-4 carbon atoms, are presently preferred. Alkenyl groups include those having 2-8 carbon atoms, both straight and branched chain, as exemplified by vinyl, allyl, methallyl, butenyl, pentenyl, hexenyl, heptenyl, octenyl, and isomeric forms thereof. The alkynyl groups include those having 2-8 carbon atoms, both straight chain and branched, as exemplified by ethynyl, propynyl, butynyl, pentynyl, hexynyl, heptynyl, octynyl and isomeric forms thereof. Cycloalkyl groups include those having 3-15 carbon atoms as exemplified by cyclopropyl, cyclobutyl, cyclopentyl, cyclohexyl, 1-cyclohexenyl, methylcyclohexenyl cycloheptyl, cyclooctyl, cyclodecyl, cycloundecyl, cyclododecyl and cyclopentadecyl. The cycloalkyl groups having 3-8 carbon atoms are presently preferred. The aryl and aralkyl groups comprehended are aromatic groups generally as exemplified by tolyl, xylyl, benzyl, phenethyl, phenylpropyl, benzhydryl, and the like, as well as fused and bridged ring structures, such as d-10-camphoryl, indanyl, indenyl, naphthyl, naphthylmethyl, acenaphthyl, phenanthyl, cyclopentanopolyhydrophenanthyl, adamantanyl, bicyclo[3:1:1]heptyl, bicyclo[2:2:2]octyl and the like. All of the above can either be unsubstituted or substituted with one or more non-interfering substituents, such as hydroxy or hydroxy derivatives; alkoxy such as methoxy, ethoxy, propoxy, butoxy, and the like; acyloxy, such as acetoxy, propionoxy, butyroxy and the like; nitro groups; alkylamino groups such as dimethylamino and the like; halogens, such as fluorine, chlorine, iodine or bromine; carbonyl derivatives such as enol ethers and ketals; and the like.

The acyloxy groups include those derived from saturated and unsaturated carboxylic acids, carbocyclic carboxylic acids and heterocyclic carboxylic acids. They include, by way of example, straight or branched chain aliphatic groups having 1-18 carbon atoms such as acetoxy, propionyloxy, butyryloxy, isobutyryloxy, palmitoyloxy, stearoyloxy and the like. Also included are the unsaturated aliphatic groups such as acryloyloxy, propioloyloxy, crotonoyloxy, oleoyloxy and the like. Examples of those group derived from the carbocyclic carboxylic acids are benzoyloxy, 2-naphthoyloxy, toluoyloxy, cinnamoyloxy and the like. Examples of those groups derived from heterocyclic carboxylic acids are 3-furoyloxy, 2-thenoyloxy, nicotinoyloxy, isonicotinoyloxy and the like. The acyloxy groups optionally can be substituted with non-interfering substituents, which may include substituents represented by Z as defined herein.

The heterocylic moieties formed by the group

when R' and R" are taken together with N, include 5-6 membered ring structures where N is a ring member. Those groups are exemplified by 1-pyrrolyl, 1-imidazolyl, 1-pyrazolyl, 1-piperidyl and the like, or fused ring compounds such as 1-indolyl, 1-H-indazol-1-yl, 3-H-indol-1-yl and the like. The heterocyclic moieties may optionally include other hetereo atoms such as oxygen and sulfur. Included therein are morpholino and thiazolyl groups.

The aryl moieties comprehended by Ar include aryl and aralkyl groups generally as described above. The aryl groups include carbocyclic radicals having from 6 to 20 carbon atoms. The carbocyclic radicals may be monocyclic as represented by the phenyl radical or they may be condensed having at least two rings with at least two carbon atoms in common. Examples of condensed aryl radicals are the naphthyl, the indenyl, the anthryl, the acenaphthyl, the indanyl and the biphenyl radicals and the like. The carbocyclic radicals can carry additional substituents, for example 1 to 3 lower alkyl radicals and/or lower alkoxy radicals and/or an alkanoyl radical with up to 12 carbon atoms and/or 1 to 3 halogen atoms, more particularly 1 to 3 fluorine, chlorine or bromine atoms and/or an aroyl radical with up to 12 carbon atoms and/or a nitro group. In addition the carbocyclic radicals can also comprise saturated or unsaturated isocylic rings. Examples of unsaturated isocyclic radicals are the phenyl, cyclohexenyl, cyclopentenyl and the naphthyl radicals. Examples of the saturated isocyclic radicals are the cyclohexyl, cyclopentyl, cycloheptyl and the cyclopropyl radicals. Additionally, the carbocyclic radicals may be linked to one or more (up to 4) rings directly by simple bonds to form a ring assembly in accordance with IUPAC Rule A-51. Such a ring assembly may include 5 to 26 carbon atoms, including the carbon atoms of the substituents. Examples of such carbocyclic ring structures include the 4-cyclohexylphenyl, the 4-biphenyl, the 3-biphenylyl, the 5-cyclohexyl-1-indanyl, the 4-(1-cyclohexen-1-yl)phenyl and the 5-phenyl-1-naphthyl radicals and the like. Those ring assemblies can carry from 1 to 3 substituents such as described above. In particular, the aryl moieties comprehended include those of acid products such as exemplified in U.S. Pat. Nos. 3,385,386; 3,660,437; 3,624,142; 3,755,427; 3,904,682; and 3,912,748 and Belgian Pat. No. 747,812. Described therein are substituted or unsubstituted phenyl, phenoxyphenyl, naphthyl or biphenyl groups, such as represented by 3-phenoxyphenyl, 2-fluoro-1,1'-biphenylyl, 4-isobutylphenyl, 4'-fluoro-4-biphenylyl, 6-methoxy-2-naphthyl, 5-bromo-6-methoxy-2-naphthyl and 4-chlorophenyl-5-benzoxazoyl.

The halogens comprehended herein are bromine, chlorine, fluorine and iodine, with bromine and chlorine being presently preferred.

Z may itself be a leaving group or a group which is convertible to a leaving group. Leaving groups include the anions of inorganic and organic acids.

Those groups are sufficiently labile to disassociate from the substrate upon and/or by contacting of the substrate with a Lewis acid, an agent having an affinity for oxygen or a protic or dipolar aprotic solvent during rearrangement of the aryl α-substituted alkyl ketal to the α-arylalkanoic acid or ester, ortho ester or amide thereof. Typical leaving groups are the halogens as exemplified by bromine, chlorine and iodine. Alternatively, Z is an anionic residue of an organic acid. Particularly suitable organic acids are those having electron deficient substituents such as exemplified by aryl, aralkyl, cycloalkyl, alkyl, alkenyl and alkynyl sulfonic acids and substituted benzoic and phosphonic acids. Presently preferred are those leaving groups wherein Z represents a group of the formula:

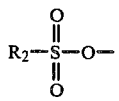

wherein $R_2$ is alkyl, cycloalkyl, alkenyl, alkynyl, aryl or aralkyl. Among such leaving groups, those in which $R_2$ is alkyl, aryl or aralkyl are especially advantageous, such as methanesulfonyloxy, benzenesulfonyloxy and p-toluenesulfonyloxy.

Groups represented by Z which can be converted to leaving groups are exemplified by hydroxy and by protected hydroxy groups such as acetoxy, benzoyloxy, trialkylsiloxy (e.g. trimethylsiloxy and triethylsiloxy) and dihydropyranyloxy. In some instances, the group represented by Z may itself be a leaving group which can be converted into a different leaving group at a subsequent stage of the process. All such variations are comprehended by Z in its broadest representation.

The organometallic reagents of formula I are conveniently prepared by conventional methods for preparing Grignard reagents. The appropriate aryl halide of the formula:

Ar—X is dissolved in an anhydrous, aprotic medium such as an ether, for example, tetrahydrofuran, diethyl ether and the like, or mixtures thereof, and added to magnesium metal. Preparative methods analogous to those described in U.S. Pat. No. 3,959,364 can be utilized. For example 2-bromo-6-methoxynaphthalene is dissolved in an ether such as tetrahydrofuran and the resulting solution added slowly to magnesium to form the magnesium Grignard of 2-bromo-6-methoxynaphthalene. The other divalent metallic derivatives, i.e. of cadmium, copper-(II), manganese and zinc, are prepared from the magnesium Grignard of the aryl halide, Ar—X, by conventional exchange procedures, such as have been described in U.S. Pat. Nos. 3,658,858 and 3,975,432. Typically, the magnesium Grignard of the aryl halide is contacted with a halide of the metal to be exchanged in a suitable solvent, such as a hydrocarbon solvent, at elevated temperatures. Whether the compound of the formula ArMX or $(Ar)_2M$ is formed depends on the amount of metal halide employed in the reaction. The compound of the formula ArMX is primarily formed when one molar equivalent of the metal halide is employed, and the compound of the formula $(Ar)_2M$ primarily is formed when one-half molar equivalent of the metal halide is employed. For example, the contacting of one molar equivalent of 2-bromo-6-methoxynaphthalene with one-half molar equivalent of zinc chloride in benzene yields a solution of di-(6-methoxy-2-naphthyl)-zinc. When one molar equivalent of zinc chloride is employed, a solution of (6-methoxy-2-naphthyl)zinc chloride is obtained. The organo lithium compounds are prepared directly from the aryl halide by contacting the aryl halide with lithium metal in a manner similar to the preparation of the magnesium Grignard. The copper(I) compound is prepared directly from the lithium derivative by reaction with cuprous bromide in an ether solvent (U.S. Pat. No. 3,658,863).

The substituted acyl halides of formula II are prepared from corresponding acids by α-halogenation of the alkanoic acid by the addition of halide in the presence of a catalytic amount of phosphorus trichloride (Hell-Volhard-Zelinsky reaction) to afford the α-haloalkanoic acid. In the case where Z is halogen, the α-haloalkanoic acid is converted directly to the desired acyl halide by reaction with thionyl chloride, phosgene, phosphorous pentachloride or the like. While other acyl halides, e.g. bromides and iodides, can be utilized, the acyl chlorides are generally satisfactory for subsequent addition to the organometallic reagent.

When Z comprises an ester leaving group such as exemplified by a group of the formula:

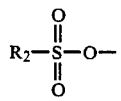

or another anionic residue of an organic acid, the α-haloalkanoic acid is hydrolyzed to the α-hydroxyalkanoic acid, esterified to form the α-hydroxyalkanoate and treated with an appropriate organic acid halide to form the diester. Subsequent hydrolysis affords the α-substituted alkanoic acid. At this stage, the α-substituent does not hydrolyze since the terminal ester group hydrolyzes much more rapidly than the α-substituent. Then the α-substituted alkanoic acid is treated with a halide such as thionyl chloride, benzenesulfonyl chloride, phosgene, phosphorus trichloride or pentachloride or the like to afford the α-substituted acyl halide, which typically is an α-substituted acyl chloride. That sequence of reactions is illustrated by the addition of bromine to propionic acid in the presence of phosphorus trichloride to afford α-bromopropionic acid. The α-bromopropionic acid is hydrolyzed with base such as potassium hydroxide, to form the α-hydroxypropionic acid which is esterified with an alcohol, e.g. ethanol, under acidic conditions to afford ethyl 2-hydroxypropionate (i.e. ethyl α-hydroxypropionate). Contacting of ethyl 2-hydroxypropionate with methanesulfonyl chloride yields ethyl 2-methanesulfonyloxypropionate, which is hydrolyzed with potassium hydroxide to afford 2-methanesulfonyloxypropionic acid. Further reaction of that material with thionyl chloride yields 2-methanesulfonyloxypropionyl chloride, which is subsequently utilized.

The optically active α-substituted acyl halides are prepared by resolution of the racemic α-hydroxyalkanoic acids or esters by conventional methods using optically active amine bases or from available amino acids, for example, such as by methods described in the *Journal of the American Chemical Society*, 76, 6054 (1954).

When α-arylpropionic acids are to be prepared by the process of this invention, a particularly advantageous starting material is lactic acid (i.e. 2-hydroxypropionic acid). The naturally occurring lactic acid, L-(+) lactic acid, is optically active and as such is a preferred starting material for the stereoselective processes described herein. Alternatively, the ethyl ester of L-(+)lactic acid also is commercially available (Pettibone World Trade, Chicago, Ill. and C. V. Chemie Combinatie, Amsterdam C.A.A., Holland) and is a convenient starting material for the optically active α-substituted propionyl halides utilized in the stereoselective process of this invention. Depending on the number of inversions at the asymmetric carbon atom of the propionic acid group during subsequent steps in the process, as will be described more fully hereinafter, either the (+)-lactic acid or the (−)-lactic acid is the preferred starting material. The (−)-lactic acid can be obtained from the racemic lactic acid by conventional resolution methods or prepared directly from glucose via a method described in Biochemical Prepn., 3, 61 (1953).

The optically active, substituted propionyl halides are prepared from the optically active ester of the appropriate lactic acid enantiomer by treating that enantiomer with an organic acid halide, such as, for example, sulfonic acid halides of the formula:

wherein $R_2$ and X are as defined above, to form the α-substituted propionate. Basic hydrolysis of the ester to the acid, such as with potassium hydroxide in aqueous methanol, and subsequent treatment with a halogenating agent, such as thionyl chloride, yields the optically active α-substituted propionyl halide. Typically, (S) ethyl 2-hydroxypropionate, corresponding to the ethyl ester of L-(+)lactic acid, is treated with methanesulfonyl chloride, in the presence of an organic base, such as triethylamine, and an inert solvent, such as toluene, to afford (S) ethyl 2-methanesulfonyloxypropionate. Basic hydrolysis of that material with potassium hydroxide in aqueous methanol yields (S) 2-methanesulfonyloxypropionic acid, which then is allowed to react with thionyl chloride to afford (S) 2-methanesulfonyloxypropionyl chloride.

In order to form the (R) substituted propionyl chloride, one begins with (R) ethyl 2-hydroxypropionate and proceeds through the above-described process sequence to obtain the (R) 2-substituted propionyl halide such as (R) 2-methanesulfonyloxypropionyl chloride.

The acyl amines represented by formula II when Y is a group of the formula:

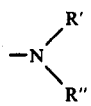

wherein R' and R" are alkyl or aryl or when taken together with N form a heterocyclic moiety which optionally can contain other hetero atoms, are prepared from the acyl halides and an N,N-disubstituted amine or the parent nitrogen containing heterocycle. For example, 2-methanesulfonyloxypropionyl chloride is contacted with dimethylamine to afford N,N-dimethyl 2-methanesulfonyloxypropionamide. Other disubstituted amines can be utilized as well. The acyl amines derived from heterocyclic amines having substantial acidic character such as the imidazoles, pyrroles, indoles and carbazoles are also considered useful.

The acyl halides can be converted to the symmetrical or mixed acid anhydrides corresponding to the compounds of formula II when Y is acyloxy, by contacting the acyl halide with an appropriate acid. For example, 2-methanesulfonyloxypropionyl chloride is allowed to react with acetic acid to afford the mixed anhydride, acetic 2-methanesulfonyloxypropionic anhydride. Additionally, for example, 2-methanesulfonyloxypropionyl chloride is allowed to react with 2-methanesulfonylotypropionic acid to afford bis(2-methanesulfonyloxypropionic)anhydride, a symmetrical anhydride. Alternatively, the acid precursors of the acyl halides of formula II can be contacted with an appropriate acyl halide to afford the symmetrical or mixed acid anhydrides. For example, 2-methanesulfonyloxypropionic acid is allowed to react with acetyl chloride to afford the mixed anhydride, acetic 2-methanesulfonyloxypropionic anhydride.

The optically active acyl amines and acid anhydrides are prepared conveniently from the optically active acyl halides in the manner described above to yield materials particularly useful in the stereospecific process of this invention.

The compounds represented by formula II also encompass compounds in which Z is a group which can be converted into a suitable leaving group at subsequent stages of the process, i.e. at some point after the compound of formula I has been allowed to react with the compound of formula II. Such groups are, for example, hydroxy, and protected hydroxy groups such as acetoxy, benzoyloxy, dihydropyranyloxy, trialkysiloxy and the like. Typically, the α-hydroxy substituent of the α-hydroxyalkanoic acid or an ester thereof is protected during the addition of the compound of formula II to the compound of formula I. Subsequently, the protecting group is removed and a suitable leaving group is generated. Typically, (S) 2-hydroxypropionic acid is treated with acetyl chloride in the presence of sulfuric acid to yield (S) 2-acetoxypropionic acid. Subsequent treatment with thionyl chloride affords (S) 2-acetoxypropionyl chloride, a compound of formula II.

The compound of formula I is allowed to react with the compound of formula II to yield a compound of the formula:

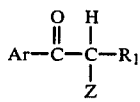

(III)

wherein Ar, $R_1$, and Z are as defined above. By employing an optically active acyl halide, acyl amine or acid anhydride of the formula II, the corresponding optically active aryl α-substituted alkyl ketone is obtained. That reaction step proceeds with substantially 100% retention of optical activity. For example, the magnesium Grignard of 2-bromo-6-methoxynaphthalene is contacted with (S) 2-methanesulfonyloxypropionyl chloride in an inert solvent such as tetrahydrofuran to yield (S) 1-(6-methoxy-2-naphthyl)-2-methanesulfonyloxypropan-1-one. The use of the (R) form of the acyl halide produces the (R) form of the ketone, e.g. (R) 1-(6-methoxy-2-naphthyl)-2-methanesulfonyloxypropan-1-one. Reaction conditions for this step of the process are not considered critical. Generally, the reaction is conducted at temperatures below room temperature. For example, the range of −70° C. to 0° C. is suitable. Inert solvents such as the ethers (e.g. tetrahydrofuran) form a convenient medium for conducting the reaction. The solvents may be used alone or as mixtures. The ratio of the acyl halide, acyl amine or acid anhydride to the organmetallic compound typically is between 1.0–1.5 equivalents, although greater excesses can be used.

The racemic and optically active ketones of the formula:

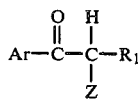

(III)

can be utilized in alternate processes to yield the desired α-arylalkanoic acids. Representative process schemes are illustrated below.

REACTION SCHEME I

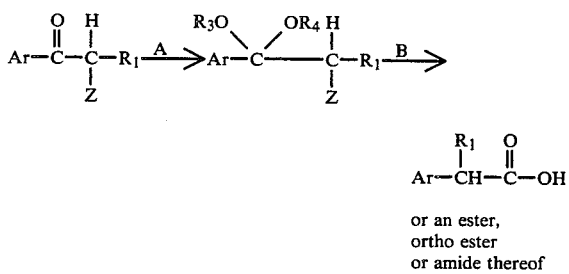

or an ester,
ortho ester
or amide thereof

In Scheme I, Ar, $R_1$ and Z are as defined above. $R_3$ and $R_4$ are alkyl having 1–8 carbon atoms, optionally the same or different, or when taken together, are alkylene having 2–8 carbon atoms.

In Reaction Scheme I, the ketalization step (step A) is conducted under conditions of retention of configuration at the asymmetric carbon atom. Typically, the ketal is formed by contacting the ketone with an ortho ester in the presence of an acid catalyst in an alcoholic solvent. Such a method utilizes trialkyl orthoformates, such as trimethyl orthoformate or triethyl orthoformate in the presence of an acid catalyst such as sulfuric acid, p-toluenesulfonic acid, ferric chloride, ammonium nitrate, ammonium chloride or acidic ion exchange resins such as Amberlyst-15, Nafion H(perfluoronated sulfonate polymer) and acidic montmorillonite clay (e.g. Girdler Ⓡ catalyst K-10, Girdler Chemicals Inc., Louisville, Ky). Typically, (S) 1-(6-methoxy-2-naphthyl)-2-methanesulfonyloxypropan-1-one is contacted with trimethyl orthoformate in the presence of sulfuric acid to yield (S) 1,1-dimethoxy-1-(6-methoxy-2-naphthyl)-prop-2-yl methanesulfonate.

Cyclic ketals are formed by using glycols and other polyhydric alcohols such as ethylene glycol, trimethylene glycol, dimethylpropylene diol and the like in the presence of an acid catalyst. The water which forms is removed by azeotropic distillation. Other useful ketalization agents are trimethylsilyl trifluoromethanesulfonate with an alkoxysilane [Tetrahedron Letters, 21, 1357–8 (1980)], 2,2-dimethoxypropane and dimethylsulfite. The ketalization agents can be used in amounts of about 1–50 molar equivalents per molar equivalent of ketone. When the orthoformates are utilized, a range of 2.0–5.0 equivalents is satisfactory. Usually about 0.5–20 percent on a molar basis of acid catalyst is utilized. Inert solvents such as alcohols, benzene, toluene and the like are utilized. When the cyclic ketals are formed from the polyhydric alcohols, a solvent such as toluene or benzene typically is used to allow azeotropic distillation of the water formed. While temperatures are not critical, temperatures in the range of 0° C. to 150° C. are typical depending on the solvent and the ketal.

When trimethyl orthoformate is utilized as the ketalization agent, the addition of an inert co-solvent such as toluene or methylene chloride appears to solubilize the ketone and lead to reduced usage of trimethyl orthoformate. A temperature range of 35° C. to 80° C. is presently preferred and about 30 percent on a molar basis of oleum gives particularly satisfactory results. Reaction times of hours to days are considered typical depending on the nature of the solvent and the temperature and the amount of ketalizing agent used.

The rearrangement step (step B) can be conducted by a variety of methods depending to some extent on the nature of the leaving group Z.

When Z is halogen, the rearrangement is conveniently conducted in an inert solvent in the presence of catalyst such as a Lewis acid (see for example European Patent Office Application No. 81200210.3, filed Feb. 23, 1981, bearing publication No. 0034871, published Sept. 2, 1981). Representative catalysts are the organic salts, such as acetate, propionate, benzoate, trifluoromethanesulfonate, methanesulfonate, and the like, and the inorganic salts such as chloride, bromide, iodide, sulfate and the like of copper, magnesium, calcium, zinc, cadmium, barium, mercury, tin, antimony, bismuth, manganese, iron, cobalt, nickel and palladium. The metal halides such as zinc chloride, cobalt chloride, zinc bromide, stannous chloride, ferrous chloride, ferric chloride, nickel bromide, cadmium chloride, magnesium chloride, mercurous chloride, mercuric chloride, antimony chloride, barium chloride, calcium chloride, cuprous chloride, cupric chloride, manganese chloride, stannic chloride, bismuth chloride and palladium trichloride are considered particularly useful. The rearrangement is conducted in a suitable solvent such as the aliphatic halohydrocarbons, aliphatic cyclic hydrocarbons, lower alcohols, aliphatic acids and esters thereof, aromatic hydrocarbons and haloaromatic hydrocarbons. Representative examples are dichloromethane, trichloromethane, chlorobenzene, toluene, methylene chloride, methanol, trimethyl orthoformate and mixtures thereof. The rearrangement is conducted in the temperature range from about 0° C. to the reflux temperature of the solvent, with due consideration given to the temperature stability of the ketal and the resulting acid or esters thereof. Reaction times are not critical and vary with the nature of the ketal and the catalyst and the reaction temperature. Times ranging from about 0.5 hours to 160 hours are considered representative. Other particulars of the rearrangement process can be found in the above-referenced European Patent Application, Publication No. 0034871, which is incorporated herein by reference.

An alternative rearrangement process when Z is halogen has been described in British Application No. 8005752, filed Feb. 20, 1980, bearing publication No. 2,042,543, published Sept. 24, 1980, and which is incorporated herein by reference. That process utilizes the silver (I) salts of organic or inorganic anions as catalysts for the rearrangement step in an acidic, alcoholic medium. The acid typically is selected from the Lewis acids, boron trifluoride, fluoroboric acid, methanesulfonic acid, sulfuric acid, the complexes $BF_3.2CH_3COOH$, $HBF_4.Et_2O$ (etherated fluoroboric acid), $BF_3.Et_2O$ (boron trifluoride etherate) and $BF_3.2CH_3OH$. The silver salts are the silver (I) salts of organic and/or inorganic anions, mixtures thereof, and silver oxide. Representative silver salts are silver acetate, $AgSbF_6$ (silver hexafluoroantimoniate), $AgClO_4$ (silver perchlorate), $AgCF_3SO_3$ (silver trifluoromethane sulfonate), $AgBF_4$ (silver tetrafluoroborate), silver nitrate, silver carbonate, silver sulfate and silver oxide. The rearrangement is conducted in a protic or dipolar, aprotic solvent, such as provided by an alcoholic medium, including the alkanols (e.g. methanol, ethanol), and cycloalkanols, and as provided by the orthoformates, acetone dimethylacetal or the $BF_3.2CH_3OH$ complex.

When Z comprises an ester leaving group of the formula:

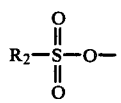

or another anionic residue of an organic acid, the ketal formed in step A is solvolyzed according to step B to the rearranged α-arylalkanoic acid or an ester, ortho ester or amide thereof, depending on the solvolysis conditions. The solvolysis is conducted under either basic, neutral or acidic conditions. Reaction times, temperatures and material ratios during the solvolysis step are not considered critical. Typically, temperatures in the range between 0° C. and 200° C. and times ranging between 1-100 hours are satisfactory. Temperatures of greater than 50° C. appear to accelerate the rearrangement. Typically, the solvolysis is effected by maintaining the ketal in contact with a protic or dipolar, aprotic solvent for a time sufficient to form the α-arylalkanoic acid or the ester, ortho ester or amide thereof. Protic solvents comprehended include water, alcohols, ammonia, amides, N-alkylamides, carboxylic acids and mixtures thereof.

Representative alcohols include primary, secondary and tertiary alcohols and polyhydric alcohols. They include alkanols, alkenols, cyclic alkanols, aromatic alcohols, glycols, and the like. Examples of the alkanols comprehended are methanol, ethanol, butanol, pentanol, hexanol, heptanol, octanol, and the branched chain isomers thereof. Examples of the alkenols are allyl alcohol, 2-buten-1-ol and the like. Cyclic alkanols are exemplified by cyclopropanol, cyclobutanol, cyclohexanol and the like. Examples of aromatic alcohols are phenol, α-naphthol, β-naphthol, p-cresol and the like. Representative amides are formamide, acetamide, propionamide, benzamide and the like. Typical of the N-alkyl amides are N-methylformamide and N-ethylformamide. Carboxylic acids are alkanoic acids such as formic acid, acetic acid, propionic acid, n-butyric acid and the branched chain isomers thereof; alkenoic acids, such as acrylic acid, maleic acid and fumaric acid and the like; aryl acids such as benzoic acid, and the like, and diacids such as phthalic acid, isophthalic acid, malonic acid, succinic acid, glutaric acid and the like.

Dipolar, aprotic solvents are typified by dimethylsulfide, acetone, dioxane, 1,2-dimethoxyethane, carbon disulfide, dialkylamides such as dimethylacetamide and dimethylformamide, nitrobenzene, nitromethane, acetonitrile and the like and mixtures thereof.

The rate of the rearrangement reaction appears to be enhanced by the presence of salts of organic or inorganic anions. For example, the addition of sodium acetate or sodium bicarbonate to the reaction mixture facilitates the reaction. Additionally, it is sometimes desirable to buffer the solvent medium to prevent hydrolysis of the ketal prior to occurance of the rearrangement. Typical buffering salts include the calcium, sodium, potassium and lithium salts of carbonate, bicarbonate, anions of organic acids and phosphates.

Depending on the nature of the protic or dipolar aprotic solvent medium, the α-arylalkanoic acid may not be directly formed. Instead, the ester, ortho ester or amide of the α-arylalkanoic acid may be formed. For example, if the solvent medium contains water, an ester of the α-arylalkanoic acid typically is formed wherein the ester group is derived from the ketal functionality or from the solvent. Mixed esters can be formed. Under anhydrous alcoholic conditions, ortho esters of the α-arylalkanoic acid can be formed wherein the ester groups may be derived from the ketal functionality or from the solvent and may be mixed. Likewise, when an amine is present in the solvent medium, formation of an amide of the α-arylalkanoic acid can be expected. Those compounds typically are not isolated but are hydrolyzed directly to the desired α-arylalkanoic acid.

Depending on the reaction conditions, hydrolysis of an ester, ortho ester or amide formed may be effected concomitantly or sequentially by standard methods. For example, when the protic solvent medium comprises acetic acid and sodium acetate and the ester substrate comprises 1,1-dimethoxy-1-(6-methoxy-2-naphthyl)prop-2-yl methanesulfonate, there is afforded the compound, methyl 2-(6-methoxy-2-naphthyl)propionate. The methyl ester is then hydrolyzed to the corresponding acid by contact with base. Alternatively, the α-arylalkanoic acid can be obtained by concomitant hydrolysis by maintaining the ester substrate in contact with a methanol-water solution containing sodium bicarbonate. Typically, 1,1-dimethoxy-1-(6-methoxy-2-naphthyl)prop-2-yl methanesulfonate is maintained in contact with a methanol-water solution containing sodium bicarbonate to afford 2-(6-methoxy-2-naphthyl)propionic acid.

When the stereoselective process described herein is utilized to produce the optically active esters of the α-arylalkanoic acids, it has been determined that the presence of excess base during the solvolytic rearrangement step can racemize the optically active ester so produced. Accordingly, it is presently desirable to minimize the amount of base which is in contact with the optically active ester. That can be accomplished by conducting the solvolysis under buffered acidic conditions or in the presence of an insoluble base, i.e. a base which is insoluble in the solvent phase containing the optically active ester, or in a weakly basic media. For example, when the solvolysis is conducted in methanol, the use of calcium carbonate or resin bases as the insoluble base gives satisfactory results. For example, when (S) 1,1-dimethoxy-1-(6-methoxy-2-naphthyl)prop-2-yl methanesulfonate is maintained in contact with an aqueous methanol solution in which calcium carbonate is stirred as an insoluble base, (S) methyl 2-(6-methoxy-2-naphthyl)propionate is obtained in greater than 95 percent optical purity. The methyl ester then is converted to (S) 2-(6-methoxy-2-naphthyl)propionic acid by acid catalysis or saponification, where such saponification is conducted in an aprotic solvent such as acetone.

The problem of isomerization in the presence of excess base appears to be due in part to the relative slowness of the rearrangement step. During solvolysis, at any one time only a small amount of sulfonic acid, e.g. methanesulfonic acid, is being formed. If an insoluble, substantially insoluble, or weak base is utilized, only a very low concentration of hydroxyl ions are present. The low concentration is sufficient to neutralize the acid formed but is insufficient to isomerize the optically active ester formed.

Alternatively, the rearrangement step (step B) can also be effected by contacting the ketal formed in step A with an agent having affinity for oxygen. Under such conditions, the ester of the α-arylalkanoic acid is produced.

The agents having an affinity for oxygen are those compounds having the ability to coordinate to accept a lone electron pair of an oxygen atom. Representative examples are iodotrialkylsilanes, such as iodotrimethylsilane, iodotriethylsilane and the like, the trialkylsilyl perfluoroalkylsulfonates such as trimethylsilyl trifluoromethanesulfonate, trimethylsilyl pentafluoroethanesulfonate and the like, and Lewis acids such as aluminum chloride, aluminum bromide, zinc chloride, stannous chloride, stannic chloride, titanium chloride, boron fluoride, ferric chloride, ferrous chloride and the other Lewis acids described previously. The agents having affinity for oxygen can be used alone or as mixtures.

The amount of the agent having an affinity for oxygen used depends to some extent on the type of the ketal being rearranged and/or on the type of the agent. Generally, it is used in an amount of about 0.1 to 5.0 moles per mole of the ketal formed in step A. A range of 1.0–2.0 moles is presently preferred.

The treatment of the ketal formed in step A with the agent having affinity for oxygen can be carried out in the absence of solvent. However, the process is conveniently carried out in a solvent, especially an aprotic solvent. For example, where a Lewis acid or an iodotrialkylsilane is used, halogenated hydrocarbons such as methylene chloride, chloroform and 1,2-dichloroethane are advantageous. When the trialkylsilyl perfluoroalkanesulfonates are used, the halogenated hydrocarbons, acetonitrile and orthoformates are presently preferred as solvents.

Reaction conditions can vary widely, although a temperature range of about −40° C. to about 150° C. is satisfactory. A range of about −20° C. to about 100° C., and especially about −10° C. to about 90° C., is presently preferred.

When the agent having affinity for oxygen is a Lewis acid, the product produced in step B may sometimes form a complex with the agent. In this case, the product may be isolated by adding water to the reaction mixture to decompose the complex. The desired product is then isolated by conventional methods, such as extraction, chromatography, distillation and crystallization.

When Z is a group which is convertible to a suitable leaving group, the conversion of Z can take place either before step A or thereafter, but before step B. For example, when the magnesium Grignard of 2-bromo-6-methoxynaphthalene is contacted with (S) 2-trimethylsiloxypropionyl chloride, (S) 1-(6-methoxy-2-naphthyl)-2-trimethylsiloxypropan-1-one is obtained. Regeneration of the hydroxyl group by hydrolysis affords (S) 2-hydroxy-1-(6-methoxy-2-naphthyl)propan-1-one. Further reaction with methanesulfonyl chloride then affords (S) 1-(6-methoxy-2-naphthyl)-2-methanesulfonyloxy propan-1-one, which is processed according to step A. Alternatively, the ketone can first be ketalized according to step A and the regeneration of the hydroxyl group and the formation of the sulfonate ester can occur subsequently but prior to step B.

When it is desired to practice the stereoselective process described herein, the particular stereoismer of the material described by the formula:

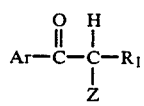

(III)

is produced to provide the desired optically active stereoisomer of the formula:

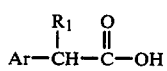

or an ester, ortho ester or amide thereof, wherein Ar, $R_1$ and Z are as defined above. In Reaction Scheme I, the ketalization step A proceeds under conditions of retention of configuration and the rearrangement step B proceeds under conditions of inversion of configuration at the asymmetric carbon atom. Accordingly, for example, when it is desired to produce (S) (6-methoxy-2-naphthyl)propionic acid, the (S) form of ethyl lactate is utilized to produce (S) 2-methanesulfonyloxypropionyl chloride in the manner described previously. Utilization of the (S)-form of that reagent with the magnesium Grignard of 6-methoxy-2-bromonaphthalene affords (S) 1-(6-methoxy-2-naphthyl)-2-methanesulfonyloxypropan-1-one. Ketalization with retention of configuration with trimethyl orthoformate in the presence of a catalytic amount of sulfuric acid yields (S) 1,1-dimethoxy-1-(6-methoxy-2-naphthylprop-2-yl methanesulfonate. Rearrangement of that material with sodium acetate and acetic acid in ethanol proceeds with inversion of configuration at the asymmetric carbon atom and affords (S) ethyl 2-(6-methoxy-2-naphthyl)propionate. That material is then hydrolyzed to the corresponding (S) acid.

Because the "sequence rule," when assigning an "R" or "S" configuration, depends on the nature of the groups attached to the asymmetric carbon atom, the absolute configuration of the starting and ending material in the rearrangement step is each "S" in the example given, even though there is inversion of configuration at the asymmetric carbon atom. The migration of the 6-methoxy-2-naphthyl group to the asymmetric carbon atom with inversion of configuration at that carbon atom dictates that notation.

When Z is a group of the formula:

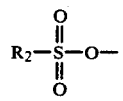

wherein $R_2$ is alkyl, cycloalkyl, alkenyl, alkynyl, aryl or aralkyl, or another anionic residue of an organic acid, step A and step B can be conveniently combined by conducting the ketalization (Step A) at elevated temperatures to effect rearrangement (step B) to the ester of the α-arylalkanoic acid. That combined ketalization-rearrangement typically is conducted at elevated temperatures in excess of 80° C. and at appropriate pressures to attain those elevated temperatures with the solvents being utilized. Typically, (S) 1-(6-methoxy-2-naphthyl)-2-methanesulfonyloxypropan-1-one is contacted with trimethyl orthoformate in the presence of 98 percent sulfuric acid in methanol and heated under 50 psi to above 80° C., to afford (S) methyl 2-(6-methoxy-2-naphthyl)propionate. Reaction times, ranging from hours to days, can vary depending on the amount of orthoformate used and the temperature at which the process is conducted. Higher temperatures may require correspondingly higher operating pressures depending on the solvents utilized.

An alternative scheme for the preparation of the α-arylalkanoic acids and esters proceeds with two inversions at the asymmetric carbon atom and is represented by the following reaction sequence:

REACTION SCHEME II

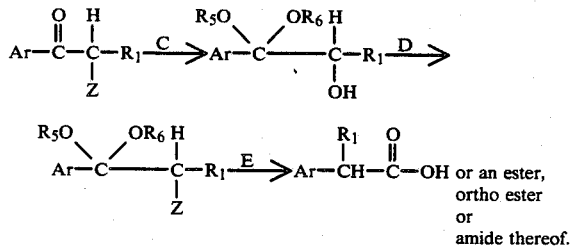

In Scheme II Ar, $R_1$ and Z are as defined above with the understanding that Z prior to step C may be the same or different than Z after step D. $R_5$ and $R_6$ are alkyl, aryl or aralkyl, optionally the same or different, or, when taken together, are alkylene having 2–8 carbon atoms. Scheme II differs from Scheme I in that the ketalization step C takes place under conditions which result in the formation of the α-hydroxy ketal with inversion of configuration at the asymmetric carbon atom. Ketalization with alkali metal alkoxides, aralkyloxides or aryloxides in an alcoholic medium yields the α-hydroxy ketals in which inversion at the asymmetric carbon atom has occurred. Representative alkali metals are sodium, potassium and lithium. The alkoxides contain 1–8 carbon atoms and are exemplified by methoxide, ethoxide and the like. Aralkyloxides and aryloxides are exemplified by benzyloxide, phenoxide and the like. Alternatively, the cyclic ketals can be formed with the polyhydric alcohols described previously in Scheme I in the presence of a catalytic amount of the alkali metal alkoxides to afford the α-hydroxy cyclic ketals in which inversion at the asymmetric carbon atom has occurred.

Regeneration of a leaving group Z in step D typically is effected by contacting the α-hydroxy ketal with an organic acid halide, such as an alkyl, alkenyl, alkynyl, cycloalkyl, aryl or aralkyl sulfonyl halide. That step occurs with retention of configuration. Rearrangement of the ester in step E takes place with inversion of configuration utilizing the methods described previously with respect to Scheme I.

Since Scheme II involves two inversions at the asymmetric carbon atom, (i.e. one inversion during the ketalization step and one inversion during the rearrangement step) the appropriate stereoisomer of the compound of the formula:

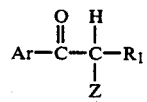

wherein Ar, $R_1$, and Z are as defined above, must be chosen to provide the desired optically active stereoisomer of the α-arylalkanoic acid being produced. For example, to produce (S) 2-(6-methoxy-2-naphthyl)propionic acid or an ester, ortho ester or amide thereof according to the procedure of Scheme II, it is necessary to begin with (R) ethyl lactate. That material is converted to (R) 2-methanesulfonyloxypropionyl chloride in the manner described herein and allowed to react with the magnesium Grignard of 2-bromo-6-methoxynaphthalene to yield (R) 1-(6-methoxy-2-naphthyl)-2-methanesulfonyloxypropan-1-one. Ketalization in step C with sodium methoxide in methanol than affords, with inversion of configuration, (S) 1,1-dimethoxy-1-(6-methoxy-2-naphthyl)propan-2-ol. Ester formation in step D occurs by contacting the (S)-ketal above with methanesulfonyl chloride to afford (S) 1,1-dimethoxy-1-(6-methoxy-2-naphthyl)prop-2-yl methanesulfonate, which is rearranged with inversion by contacting with sodium acetate and acetic acid to afford (S) methyl 2-(6-methoxy-2-naphthyl)propionate. The foregoing example is again illustrative of the peculiarities of the "sequence rule" of nomenclature, which, when utilized to assign absolute configurations to asymmetric carbon atoms, can result in an (S)-compound being converted to another (S)-compound even though inversion at the asymmetric carbon atom has occurred. That apparent inconsistency is in reality no inconsistency at all because the assignment of the "R" or "S" configuration depends on the nature of the groups attached to the asymmetric carbon atom.

The foregoing illustration is representative of the situation wherein the leaving group Z prior to step C is the same as the leaving group Z prior to step E. The leaving group Z in each instance need not be identical. For example, Z prior to step C can be a halogen, such as bromo and chloro, which is eliminated in the formation of the α-hydroxyketal. Then, the α-hydroxyketal can be contacted with methanesulfonylchloride to yield the ketal wherein the leaving group Z is methanesulfonyloxy.

The ketones of the formula III wherein Z is halogen can also be prepared from compounds prepared from (R), (S) or (RS) lactic acid or the esters thereof. In this aspect of the invention, the compounds of formula III wherein Z is a group of the formula:

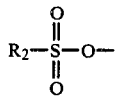

wherein $R_2$ is as previously defined are contacted with an alkali metal halide to yield the optically active or racemic compound of formula III in which Z is halogen. Typically, lithium bromide or lithium chloride is used, or a phase transfer catalyst is employed with potassium bromide in a non-polar organic solvent such as toluene. In certain solvents the reaction proceeds with racemization at the asymmetric carbon atom and as such is not universally suitable for the preparation of the optically active α-halo ketones. For example, (R) 1-(6-methoxy-2-naphthyl)-2-methanesulfonyloxypropan-1-one is contacted with lithium bromide in dimethylformamide to afford substantially all (RS) 2-bromo-1-(6-methoxy-2-naphthyl)propan-1-one. That material is suitable for use in Reaction Scheme I to produce racemic 2-(6-methoxy-2-naphthyl)propionic acid. Similarly, (S) 1-(6-methoxy-2-naphthyl)-2-methanesulfonyloxy-propan-1-one is contacted with lithium bromide to afford (RS) 2-bromo-1-(6-methoxy-2-naphthyl)propan-1-one, which is suitable for use in Reaction Scheme II to produce racemic 2-(6-methoxy-2-naphthyl)propionic acid.

In still another alternate process, the compounds of formula III can be processed according to the following Scheme III:

REACTION SCHEME III

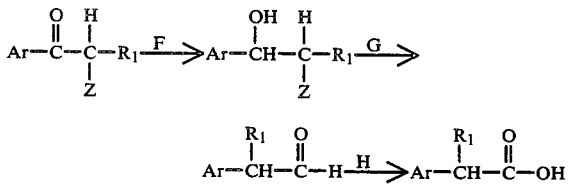

In Scheme III, Ar, $R_1$ and Z are as defined above. In step F the aryl alkyl ketone is reduced to the corresponding alcohol by catalytic hydrogenation or with metal hydrides. Catalytic hydrogenation is conveniently effected with hydrogen in the presence of a catalyst such as platinum, palladium, Raney nickel, copper chromite and the like. Convenient metal hydrides are exemplified by the borohydrides such as sodium borohydride and the aluminum hydrides such as lithium aluminum hydride. Times and temperatures will vary with the reducing agent utilized and are conventional. Typically, hydrogenation can be conducted at a temperature in a range from about 15° to 200° C. and at pressures of one atmosphere or more. The metal hydride reductions typically are conducted in ethers, dilute aqueous and/or alcoholic acids, water, alcoholic solvents, and mixtures thereof. Sodium borohydride is an especially convenient reducing agent since it rapidly reduces the ketone moiety while being relatively inert to other substituents in the substrate.

The alcohol formed in step F is rearranged in step G to the corresponding aldehyde by the methods of rearrangement described previously for Schemes I and II. The aldehyde is oxidized by conventional methods to the corresponding acid in step H. A typical oxidation is the chromic acid oxidation described in U.S. Pat. No. 3,736,767. Other oxidation agents, such as sodium chlorite, may be used as well.

Representative of Scheme III is the reaction of 1-(6-methoxy-2-naphthyl)-2-methanesulfonyloxypropan-1-one with sodium borohydride in methanol to yield 1-hydroxy-1-(6-methoxy-2-naphthyl)prop-2-yl methanesulfonate. Treating that material with sodium acetate in acetic acid affords 2-(6-methoxy-2-naphthyl)-propanal, which is oxidized with sodium chlorite to 2-(6-methoxy-2-naphthyl)propionic acid. By employing the optically active (S) 1-(6-methoxy-2-naphthyl)-2-methanesulfonyloxypropan-1-one there is obtained, following the same sequential steps, (S) 2-(6-methoxy-2-naphthyl)propionic acid.

Because application of the "sequence rule" of nomenclature depends on the nature of the groups attached to the asymmetric carbon atom in assigning an (R) or (S) configuration to that carbon atom, it is not possible to state generally that an optically active substituted acyl halide, acyl amine or acid anhydride denoted as (S) will produce an (S) or an (R) product. It can be seen from what has been described previously, that depending on the number of inversions occuring at the asymmetric carbon atom, one may want to begin with an (S) or an (R) substituted acyl halide, acyl amine or acid anhydride in the practice of this invention. However, in view of this disclosure it is considered to be well within the skill of those in the art to which this invention pertains to choose the appropriate optically active starting material to arrive at the desired optically active product.

The present invention is also directed to an optically active stereoisomer of a compound of the formula

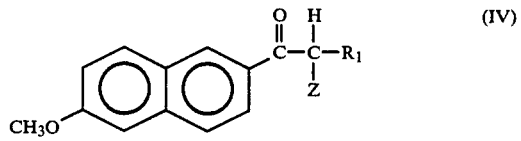

wherein $R_1$ is alkyl or cycloalkyl and Z is a leaving group, in the substantial absence of any other stereoisomer of that compound. In the context of this invention, the single stereoisomer of the above-described compounds of formula IV can correspond to 100% optical purity. However, due to the nature of chemical reactions, a certain amount of another stereoisomer of the compound may be present at the conclusion of the stereoselective preparation due to a small amount of isomerization to the undesired stereoisomer. Accordingly, for the purposes of this invention, the desired optically active stereoisomer is considered to exist in the substantial absence of any other stereoisomers of the compound if the desired optically active stereoisomer has an optical purity of 90% or more.

In the majority of instances, only a single center of asymmetry is present in the compounds of formula IV and only two stereoisomers, i.e., the enantiomers, will be present. In those instances, the optically active enantiomer of a compound of formula IV will be present in the substantial absence of the other enantiomer. In another instance, more than one center of asymmetry may exist in the compounds of formula IV. In that instance, the optically active diastereomer will be present in the substantial absence of any other diastereomer of a compound of formula IV.

For example, when Z is methanesulfonyloxy and $R_1$ is methyl, the compound of formula IV will consist of two optically active enantiomers, i.e., (R) 1-(6-methoxy-2-naphthyl)-2-methanesulfonyloxypropan-1-one; and (S) 1-(6-methoxy-2-naphthyl)-2-methanesulfonyloxypropan-1-one.

In this example, an aspect of this invention (useful in the process of Scheme I outlined above) is a material containing (S) 1-(6-methoxy-2-naphthyl)-2-methanesulfonyloxypropan-1-one in the substantial absence of (R) 1-(6-methoxy-2-naphthyl)-2-methanesulfonyloxypropan-1-one.

Another aspect of this invention (useful in the process of Scheme II outlined above) is a material containing (R) 1-(6-methoxy-2-naphthyl)-2-methanesulfonyloxypropan-1-one in the substantial absence of (S) 1-(6-methoxy-2-naphthyl)-2-methanesulfonyloxypropan-1-one.

However, when Z is d-10-camphorsulfonyloxy and $R_1$ is methyl, the compound of formula IV consists of two diastereomers which are not mirror images of each other (i.e., not enantiomers). In those instances, the composition of the invention consists of one diastereomer in the substantial absence of the other diastereomer.

While the stereoselective process of this invention is primarily utilized to produce an optically active product, which is present as a single stereoisomer in the substantial absence of any other stereoisomer of the product, thus eliminating subsequent resolution steps, the production of a product enriched in or having a major amount of the single stereoisomer as compared to any other stereoisomer of the product is also useful since the economics of any necessary resolution are improved over the case where a racemic mixture is being resolved.

As described previously, the compounds of formula IV are prepared by reacting an optically active substituted acyl halide, acyl amine or acid anhydride with the Grignard of 2-bromo-6-methoxynaphthalene in an ethereal solvent such as tetrahydrofuran, ethyl ether and the like or mixtures thereof. The preparation of the optically active acyl halides, acyl amines and acid anhydrides has been described previously herein.

The present invention is also directed to an optically active stereoisomer of a compound of the formula:

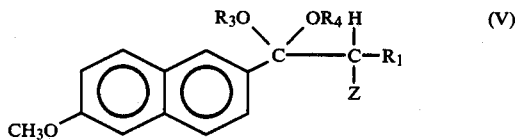

wherein $R_1$ is alkyl having 1-8 carbon atoms, $R_3$ and $R_4$ are alkyl having 1-8 carbon atoms, optionally the same or different, or when taken together, are alkylene having 2-8 carbon atoms, and Z is halogen, hydroxy, acetoxy, benzoyloxy, dihydropyranyloxy, trialkylsiloxy or a group of the formula:

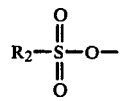

wherein $R_2$ is alkyl, cycloalkyl, alkenyl, alkynyl, aryl or aralkyl, but not d-10-camphoryl when $R_3$ and $R_4$ are methyl, in the substantial absence of any other stereoisomer of that compound. When only one center of asymmetry is present in a compound of formula V, the composition consists of a single enantiomer of that compound in the substantial absence of the other enantiomer. When two or more centers of asymmetry are present in a compound of formula V, the composition consists of a single diastereomer in the substantial absence of any other diastereomer of that compound. For the purposes of this invention, the desired optically active stereoisomer is considered to exist in the substantial absence of any other stereoisomers of the compound if the desired optically active stereoisomer has an optical purity of 90% or more.

Any single enantiomer or diastereomer can be utilized in the stereoselective process described herein depending on whether a single or multiple inversion takes place during the sequence of reaction steps to obtain the desired 2-(6-methoxy-2-naphthyl)alkanoic acid.

The invention is further exemplified by the embodiments described in the following illustrative and non-limiting examples.

EXAMPLE 1

120 Grams of (S) ethyl lactate and 120 grams of triethylamine are dissolved in 500 ml. of toluene, with stirring, and the solution is cooled to about 10°-15° C. Then, 120 grams of methanesulfonyl chloride are added slowly over a 1½ hour period while maintaining the temperature in the range of 10°-15° C. The formation of triethylamine hydrochloride as a precipitate is observed. The solution then is allowed to warm to about 20° C. and is poured into water. The aqueous and organic layers are separated and the organic layer is dried over magnesium sulfate and evaporated. The residue remaining is distilled at about 110° C. under 2 mm. Hg to afford 161 grams of (S) ethyl 2-methanesulfonyloxypropionate displaying an optical rotation of $[\alpha]_{25}^D = -44°$. That compound displays a characteristic NMR spectra of $\delta = 1.28$ (triplet, J=2.2), 1.57 (doublet, J=2.3), 3.12, 4.23 (quartet, J=2.2), 5.12 (quartet, J=2.3).

EXAMPLE 2

A solution of 75 grams of (S) ethyl 2-methanesulfonyloxypropionate in 250 ml. of methanol and 100 ml. of water is cooled to about 15° C. A 40% aqueous sodium hydroxide solution is slowly added to the above solution to maintain the pH at about 10.5. The reaction proceeds with rapid fall of pH and continued additions of the sodium hydroxide solution are made until the pH falls very slowly or is substantially constant. Then, concentrated hydrochloric acid is added until a pH of 1.9 is obtained. The methanol is removed under reduced pressure and the aqueous layer remaining is extracted with methylene chloride. The organic extract is evaporated to yield, as an oil, 49 grams of (S) 2-methanesulfonyloxypropionic acid, displaying an optical rotation of about $[\alpha]_{25}^D = -53.3°$.

EXAMPLE 3

84.85 Grams of (S) ethyl 2-methanesulfonyloxypropionate is dissolved in a solution of 180 ml. of methanol and 80 ml. of water, and the resultant solution is cooled to below $-15°$ C. Then an aqueous 35% sodium hydroxide solution is added slowly to maintain the pH at less than or equal to 10.5 and the addition is continued until the pH remains substantially constant. Concentrated hydrochloric acid is added to acidify the solution to a pH of about 1.8 and the methanol is evaporated under reduced pressure. The aqueous layer is extracted with ethyl acetate several times, and the organic extracts are dried over magnesium sulfate. Evaporation of the organic extract to dryness affords 51 grams of (S) 2-methanesulfonyloxypropionic acid, exibiting an optical rotation in methylenechloride of $[\alpha]_{25}^D = -54°$. That compound is crystallized from toluene and exhibits a melting point of 72°–75° C. and a characteristic NMR spectra of $\delta = 1.62$ (doublet, J=2.3), 3.09, 5.11 (quartet, J=2.3), 10.

EXAMPLE 4

A mixture containing 40 grams of (S) 2-methanesulfonyloxypropionic acid, 32 grams of thionyl chloride and one drop of dimethylformamide is heated to about 50° C., at which temperature gas evolution is observed. The mixture is slowly heated to about 70° C. and maintained at that temperature for about 1 hour. Distillation at 110° C. under 1.5 mm. Hg affords 31.2 grams of (S) 2-methanesulfonyloxypropionyl chloride, exhibiting an optical rotation in methylene chloride of $[\alpha]_{25}^D = -36.9°$. That compound exhibits a characteristic NMR spectra of $\delta = 1.68$ (doublet, J=2.3), 3.15, 5.25 (quartet, J=2.3).

EXAMPLE 5

By substituting an equivalent quantity of thionyl bromide in Example 4 and otherwise following the procedure of that Example there is obtained (S) 2-methanesulfonyloxypropionyl bromide.

EXAMPLE 6

By substituting an equivalent quantity of p-toluenesulfonyl chloride in Example 1 and following the procedure of that Example with heating at 60° C. for 8 hours, and subsequently proceeding according to the manner described in Examples 3 and 4, there is obtained (S) 2-p-toluenesulfonyloxypropionyl chloride. That compound exhibits an $[\alpha]_{25}^D = -32°$ in chloroform and a characteristic NMR spectra of $\delta = 1.18$ (triplet, J=2.2), 1.48 (doublet, J=2), 2.45, 4.13 (quartet, J=2.2), 4.96 (quartet, J=2), 7.28–8.03 (multiplet).

EXAMPLE 7

By substituting an equivalent quantity of benzenesulfonyl chloride for the methanesulfonyl chloride of Example 1, and proceeding according to that Example with heating at 30°–40° C. for 5–6 hours and subsequently following the procedure of Examples 3 and 4, there is obtained (S) 2-benzenesulfonyloxypropionyl chloride.

EXAMPLE 8

By substituting an equivalent quantity of (R) ethyl lactate in the procedure of Example 1 and otherwise following that procedure and those described in Examples 2 and 4, there is obtained (R) 2-methanesulfonyloxypropionyl chloride.

EXAMPLE 9

10 Grams of 2-bromo-6-methoxynaphthalene dissolved in 40 ml. of tetrahydrofuran are slowly added to 3.6 grams of magnesium metal at the refluxing temperature of tetrahydrofuran (about 60°–62° C.). After the addition is completed, the mixture is stirred at reflux for about 1 hour and the excess magnesium is removed by filtration to afford the Grignard solution [(6-methoxy-2-naphthyl)magnesium bromide in tetrahydrofuran].

EXAMPLE 10

The solution of (6-methoxy-2-naphthyl)magnesium bromide prepared in Example 9 is slowly added to 8 grams of (S) 2-methanesulfonyloxypropionyl chloride dissolved in 40 ml. of tetrahydrofuran which has been cooled to $-40°$ C., while keeping the temperature of the reaction mixture of about $-40°$ C. The mixture is stirred for an additional hour at that temperature and poured into 200 ml of 5% aqueous hydrochloric acid. 100 Ml. of ethyl ether is added to the reaction mixture. The precipitate is recovered by filtration and washed with 30 ml. of ice cold ethyl ether to yield 6.46 grams of (S) 2-methanesulfonyloxy-1-(6-methoxy-2-naphthyl)-propan-1-one, melting at 149°–151° C. and displaying an optical rotation in chloroform of $[\alpha]_{25}^D = -33°$. That compound displays a characteristic NMR spectra in deutorochloroform of $\delta = 1.65$ (doublet, J=2.1), 3.10, 3.9, 6.17 (quartet, J=2.1), 8.55–7.10 (multiplet).

EXAMPLE 11

Substitution of an equivalent quantity of (S) 2-p-toluenesulfonyloxypropionyl chloride in the procedure of Example 10 and conducting the coupling at $-78°$ C. affords (S) 1-(6-methoxy-2-naphthyl)-2-p-toluenesulfonyloxypropan-1-one. That compound exhibits a melting point of about 117°–119° C., an $[\alpha]_{25}^D = +24.2°$ in chloroform and a characteristic NMR spectra of $\delta = 1.67$ (doublet, J=2.2), 2.37, 3.98, 5.92 (quartet, J=2.2), 7.14–8.44 (multiplet).

EXAMPLE 12

Substitution of an equivalent quantity of (S) 2-benzenesulfonyloxypropionyl chloride in the procedure of Example 10 affords (S) 2-benzenesulfonyloxy-1-(6-methoxy-2-naphthyl)propan-1-one.

EXAMPLE 13

Substitution of an equivalent quantity of (R) 2-methanesulfonyloxypropionyl chloride in the procedure of Example 10 affords (R) 2-methanesulfonyloxy-1-(6-methoxy-2-naphthyl)propan-1-one.

EXAMPLE 14

Substitution of an equivalent quantity of (R) 2-p-toluenesulfonyloxypropionyl chloride in the procedure of Example 10 affords (R) 1-(6-methoxy-2-naphthyl)-2-p-toluenesulfonyloxypropan-1-one.

EXAMPLE 15

Substitution of an equivalent quantity of (R) 2-benzenesulfonyloxypropionyl chloride in the procedure of Example 10 affords (R) 2-benzenesulfonyloxy-1-(6-methoxy-2-naphthyl)propan-1-one.

EXAMPLE 16

A slurry of 4.6 grams of (S) 2-methanesulfonyloxy-1-(6-methoxy-2-naphthyl)propan-1-one in 50 ml. of methanol is treated with 50 grams of trimethyl orthoformate and 2 g of concentrated sulfuric acid. The mixture is heated to about 55° C. and maintained at that temperature for about 15 hours. Then the mixture is cooled and poured into aqueous sodium bicarbonate and extracted with 120 ml. of ethyl ether. The organic layer is separated and dried over magnesium sulfate and filtered. Evaporation of the ether under reduced pressure affords 4.8 grams of (S) 1,1-dimethoxy-1-(6-methoxy-2-naphthyl)prop-2-yl methanesulfonate, melting at about 112°–115° C. and displaying an optical rotation of $[\alpha]_{25}^D = -23.9°$ (c=1, chloroform). That compound displays a characteristic NMR spectra in deuterochloroform of $\tau = 9.0$ (doublet, J=2), 6.85, 6.70, 6.61, 6.07, 4.89 (quartet, J=2), 1.99–2.88 (multiplet).

EXAMPLE 17

To a solution of 7 grams of sodium acetate in 50 ml. of acetic acid is added 3 grams of (S) 1,1-dimethoxy-1-(6-methoxy-2-naphthyl)prop-2-yl methanesulfonate. The mixture is heated to about 110° C. for about 1.5 hours and then poured into 300 ml. of water. The precipitate is recovered by filtration and washed with methanol to afford (S) methyl 2-(6-methoxy-2-naphthyl)propionate, melting at about 85°–87° C. and displaying an optical rotation of $[\alpha]_{25}^D = +65.4°$ (c=1, chloroform). That material is about 92% optically pure.

EXAMPLE 18

Substitution of an equivalent quantity of (S) 1-(6-methoxy-2-naphthyl)-2-p-toluenesulfonyloxypropan-1-one in Example 16 and proceeding according to that Example affords (S) 1,1-dimethoxy-1-(6-methoxy-2-naphthyl)prop-2-yl p-toluenesulfonate. Treatment of that material in a manner similar to that described in Example 17 affords (S) methyl 2-(6-methoxy-2-naphthyl)propionate.

EXAMPLE 19

Substitution of an equivalent quantity of (S) 2-benzenesulfonyloxy-1-(6-methoxy-2-naphthyl)propan-1-one in the procedure of Example 16 and proceeding according to that Example affords (S) 1,1-dimethyl-1-(6-methoxy-2-naphthyl)prop-2-yl benzenesulfonate. Treatment of that material in a manner similar to that described in Example 17 affords (S) methyl 2-(6-methoxy-2-naphthyl)propionate.

EXAMPLE 20

The (R) 2-methanesulfonyloxy-1-(6-methoxy-2-naphthyl)-propan-1-one prepared in Example 13 is treated with a 1.5 molar excess of sodium methoxide in methanol solution. That mixture is stirred for about 1 hour at room temperature and the methanol is stripped from the mixture at about 50° C. on a rotary evaporator until approximately 80% of the methanol has been removed. The resulting reaction mixture is quenched in water and extracted with methylene chloride. The organic layer is separated, dried over magnesium sulfate and evaporated under reduced pressure to afford (S) 1,1-dimethyl-1-(6-methoxy-2-naphthyl)propan-2-ol. That material is dissolved in methylene chloride containing triethylamine and the reaction mixture is cooled to about 5° C. and one equivalent of methanesulfonyl chloride is added slowly, maintaining the temperature between 5°–10° C. After the addition of the methanesulfonyl chloride has been completed, the reaction mixture is stirred for an additional ½ hour. Then the solution is filtered to remove the triethylamine hydrochloride crystals and the filtrate is poured into water. The organic layer is separated and dried over magnesium sulfate. Evaporation of the organic layer under reduced pressure affords (S) 1,1-dimethoxy-1-(6-methoxy-2-naphthyl)prop-2-yl methanesulfonate. That material is treated in a manner similar to Example 17 to afford (S) methyl 2-(6-methoxy-2-naphthyl)propionate.

EXAMPLE 21

An equivalent quantity of each of the following materials: (S) 2-chloropropionyl chloride, (S) 2-bromopropionyl chloride, (R) 2-chloropropionyl chloride and (R) 2-bromopropionyl chloride prepared by the method of Fu et al, JACS, 76,6054 (1954) is substituted for (S) 2-methanesulfonyloxypropionyl chloride in Example 10, and the procedure of that Example is otherwise followed to afford, respectively.

(S) 2-chloro-1-(6-methoxy-2-naphthyl)propan-1-one,
(S) 2-bromo-1-(6-methoxy-2-naphthyl)propan-1-one,
(R) 2-chloro-1-(6-methoxy-2-naphthyl)propan-1-one, and
(R) 2-bromo-1-(6-methoxy-2-naphthyl)propan-1-one.

EXAMPLE 22

The following compounds are prepared from the compounds of Example 21 in a manner similar to that described in European Patent Office Application No. 81200210.3, filed Feb. 23, 1981 [EPO publication number 0034871, published Sept. 2, 1981]:

(a) From (S) 2-chloro-1-(6-methoxy-2-naphthyl)propan-1-one:
  (1) (S) 2-chloro-1,1-dimethoxy-1-(6-methoxy-2-naphthyl)propane
  (2) (S) 2-chloro-1,1-diethoxy-(6-methoxy-2-naphthyl)propane
  (3) (S) 2-chloro-1-(6-methoxy-2-naphthyl)propan-1-one ethylene acetal
  (4) (S) 2-chloro-1-(6-methoxy-2-naphthyl)propan-1-one propylene acetal
  (5) (S) 2-chloro-1-(6-methoxy-2-naphthyl)propan-1-one 1,2-dimethylethylene acetal
(b) From (S) 2-bromo-1-(6-methoxy-2-naphthyl)propan-1-one:
  (1) (S) 2-bromo-1,1-dimethoxy-(6-methoxy-2-naphthyl)propane
  (2) (S) 2-bromo-1,1-diethoxy-(6-methoxy-2-naphthyl)propane
  (3) (S) 2-bromo-1-(6-methoxy-2-naphthyl)propan-1-one ethylene acetal
  (4) (S) 2-bromo-1-(6-methyoxy-2-naphthyl)propan-1-one propylene acetal
  (5) (S) 2-bromo-1-(6-methoxy-2-naphthyl)propan-1-one 1,2-dimethylethylene acetal.

EXAMPLE 23

The materials prepared in Example 22 are each rearranged in a manner similar to that described in EPO Application No. 81200210.3, filed Feb. 23, 1981 [EPO publication no. 0034871, published Sept. 2, 1981], with the following Lewis acids: barium chloride, bismuth chloride, calcium chloride, cadmium chloride, cobalt chloride, cuprous chloride, ferrous chloride, ferric chloride, mercurous chloride, magnesium chloride, manganese bromide, manganese chloride, nickel bromide, paladium chloride, antimony chloride, stannous chloride, stannic chloride, zinc bromide, zinc chloride and zinc diacetate: to afford, after hydrolysis of any ester formed, (S) 2-(6-methoxy-2-naphthyl)propionic acid.

EXAMPLE 24

The following compounds prepared in Example 21: (R) 2-chloro-1-(6-methoxy-2-naphthyl)propan-1-one and (R) 2-bromo-1-(6-methoxy-2-naphthyl)propan-1-one are each allowed to react with at least one equimolar amount of sodium methoxide in at least one equimolar amount of methanol, to afford in each instance, (S) 1,1-dimethoxy-1-(6-methoxy-2-naphthyl)propan-2-ol.

EXAMPLE 25

(S) 1,1-dimethoxy-1-(6-methoxy-2-naphthyl)propan-2-ol is treated with a molar excess (up to 50% excess) of methanesulfonyl chloride in the presence of a molar excess of triethylamine (equal to or greater than the molar excess of methanesulfonyl chloride) in methylene chloride to afford (S) 1,1-dimethoxy-1-(6-methoxy-2-naphthyl)prop-2-yl methanesulfonate. That material is converted to (S) methyl 2-(6-methoxy-2-naphthyl)propionate in a manner similar to that described in Example 17.

EXAMPLE 26

(S) 1,1-dimethoxy-1-(6-methoxy-2-naphthyl)propan-2-ol is treated with a molar excess of p-toluenesulfonyl chloride in the presence of a molar excess of triethylamine in a manner similar to Example 25 to yield (S) 1,1-dimethoxy-1-(6-methoxy-2-naphthyl)prop-2-yl p-toluenesulfonate. That material is converted to (S) methyl 2-(6-methoxy-2-naphthyl)propionate in a manner similar to that described in Example 17.

EXAMPLE 27

The process described in Example 26 is repeated by substituting benzenesulfonyl chloride for the p-toluenesulfonyl chloride recited in that Example to afford (S) 1,1-dimethoxy-1-(6-methoxy-2-naphthyl)-prop-2-yl benzenesulfonate. That material is converted to (S) methyl 2-(6-methoxy-2-naphthyl)propionate in a manner similar to that described in Example 17.

EXAMPLE 28

A solution containing 6 ml. of anhydrous methylene chloride and 1.0 millimole of (S) 1,1-dimethoxy-1-(6-methoxy-2-naphthyl)prop-2-yl p-toluenesulfonate is added dropwise to a stirred mixture of 0.20 ml. of iodotrimethylsilane and one drop of cyclohexene in 8 ml. of anhydrous methylene chloride at room temperature under an argon atmosphere. The mixture is stirred for about 1 hour at room temperature and 10 ml. of saturated aqueous sodium bicarbonate is added. The organic and aqueous layers are separated and the organic layer is washed successively with 5 ml. of 10% aqueous sodium thiosulfate, 5 ml. of water, 5 ml. of aqueous sodium bicarbonate and 5 ml. of water. Then the organic layer is dried over magnesium sulfate to afford, upon evaporation of the solvent, (S) methyl 2-(6-methoxy-2-naphthyl)propionate.

EXAMPLE 29

In a manner similar to that employed in Example 28, (S) 1,1-dimethoxy-1-(6-methoxy-2-naphthyl)prop-2-yl p-toluenesulfonate is converted to (S) methyl 2-(6-methoxy-2-naphthyl)propionate.

EXAMPLE 30

In a manner similar to that described in Example 28, (S) 1,1-dimethoxy-1-(6-methoxy-2-naphthyl)prop-2-yl benzenesulfonate is converted to (S) methyl 2-(6-methoxy-2-naphthyl)propionate.

EXAMPLE 31

The materials prepared in Example 22 are each rearranged in a manner similar to that described in British Pat. No. 8005752, filed Feb. 20, 1980 [publication No. 2042543, published Sept. 24, 1980] with the following silver salts:
 (1) silver tetrafluoroborate and $BF_3.2CH_3OH$
 (2) silver carbonate and $BF_3.2CH_3OH$
 (3) silver acetate and $BF_3.2CH_3OH$
 (4) silver oxide and $BF_3.2CH_3OH$
 (5) silver tetrafluoroborate in methanol.
to yield, after hydrolosis of any ester formed, (S) 2-(6-methoxy-2-naphthyl)propionic acid.

EXAMPLE 32

A slurry of 2 grams of (S) 2-methanesulfonyloxy-1-(6-methoxy-2-naphthyl)propan-1-one in 35 ml. of methanol is cooled to 10° C. and 0.21 grams of sodium borohydride are added in four portions while maintaining the temperature at about 10° C. That mixture is stirred for 1½ hours, poured into an aqueous 10% acetic acid solution and extracted with methylene chloride. The organic and aqueous phases are separated and the organic phase is washed with aqueous sodium bicarbonate solution and dried over magnesium sulfate. Evaporation of the solvent affords (S) 1-hydroxy-1-(6-methoxy-2-naphthyl)prop-2-yl methanesulfonate, as a solid. That compound displays a characteristic NMR spectra in deuterochloroform of $\delta=1.2$ (doublet, $J=2$), 2.91, 3.44 (doublet, $J=2.2$), 3.87, 4.80 (multiplet, $J=2.2,2$), 7.7–7.1 (multiplet).

EXAMPLE 33

A mixture prepared from 1.2 grams of (S) 1-hydroxy-1-(6-methoxy-2-naphthyl)prop-2-yl methanesulfonate prepared according to Example 32, 20 ml. of acetic acid and 1.6 grams of sodium acetate is heated to about 45° C. and maintained at that temperature for about 6½ hours. The mixture is poured into water and extracted with ethyl ether. The ethereal layer is washed several times with water, once with aqueous sodium bicarbonate solution, and dried over magnesium sulfate. Evaporation of the ethyl ether yields, as an oil, (S) 2-(6-methoxy-2-naphthyl)propanal. That material crystallizes upon standing and exhibits a melting point of about 71°–72° C. and an $[\alpha]_{25}^D = +37°$.

EXAMPLE 34

Equivalent quantities of (S) 2-benzenesulfonyloxy-1-(6-methoxy-2-naphthyl)propan-1-one and 1-(6-methoxy-2-naphthyl)-2-p-toluenesulfonyloxypropan-1-one are each processed according to the procedures outlined in Examples 32 and 33 to afford, in each instance, (S) 2-(6-methoxy-2-naphthyl)propanal.

EXAMPLE 35

A mixture of 90 grams of ethylene glycol, 30 grams of (S) 1-(6-methoxy-2-naphthyl)-2-methanesulfonyloxypropan-1-one, 6 grams of p-toluenesulfonic acid monohydrate and 400 ml. of toluene is heated to reflux. An azeotrope of toluene, water and ethylene glycol is removed, and the water and ethylene glycol separate upon cooling and are removed via a Dean Stark trap. The reaction mixture is azeotropically dried for 5 hours and then cooled. The cooled mixture is poured into excess aqueous sodium bicarbonate, and the toluene layer is separated and dried over magnesium sulfate.

The toluene is removed by evaporation and the solid remaining is stirred in methanol to yield, after filtration, (S) 1-(6-methoxy-2-naphthyl)-2-methanesulfonyloxypropan-1-one ethylene acetal, displaying an optical rotation of $[\alpha]_{25}^D = +6.1°$ (C=1, chloroform. That compound displays a characteristic NMR spectra in deuterochloroform of $\delta = 1.35$ (doublet, J=2), 2.78, 3.83, 3.98–3.68 (multiplet), 4.28–4.0 (multiplet), 4.98 (quartet, J=2), 8–7 (multiplet).

EXAMPLE 36

A suitable pressure reactor is charged with 6.4 grams of (S) 1-(6-methoxy-2-naphthyl)-2-methanesulfonyloxypropan-1-one ethylene acetal, 60 ml. of 1,2-diethoxyethane, 50 ml. of water and 3 grams of calcium carbonate. The mixture is heated while being stirred at 120° C. for 36 hours at 42 psi. Then the mixture is cooled and the calcium salts removed by filtration. Concentrated hydrochloric acid is added and the mixture is reheated to 95° C. for 3 hours. Then the 1,2-diethoxyethane is removed by distillation to yield a solid which is extracted with ethyl ether. The organic layer is back extracted with aqueous sodium bicarbonate and the aqueous and organic layers are separated. The aqueous layer is acidified with hydrochloric acid to afford, after filtration, (S) 2-(6-methoxy-2-naphthyl)propionic acid, exhibiting a melting point of 147° C.–150° C. and an optical rotation of $[\alpha]_{25}^D = +62.2°$ in chloroform.

EXAMPLE 37

The procedure of Example 36 is repeated using dimethylformamide in place of the 1,2-dimethoxyethane. The mixture is heated to 110° C. at atmospheric pressure for 24 hours. After workup, there is obtained (S) 2-hydroxyethyl 2-(6-methoxy-2-naphthyl)propionate by preparative TLC. That material exhibits an $[\alpha]_{25}^D = +72.5°$. That material exhibits a characteristic NMR spectra in deuterochloroform of $\delta = 1.49$ (doublet, J=2.3), 3.67 (multiplet), 3.85, 3.89 (quartet, J=2.3), 4.17 (multiplet), 7.77–7.07 (multiplet).

EXAMPLE 38

A solution of 20.98 mmoles of (S) 2-methanesulfonyloxypropionic acid, 20.95 mmoles of triethylamine and 48 ml. of anhydrous tetrahydrofuran is prepared in a dry vessel under nitrogen and cooled to −30° C. The solution is stirred for about 5 minutes at −30° C., and then 231.23 mmoles of trimethylacetyl chloride are added. A white precipitate is observed. The mixture is allowed to warm to −20° C., and it is stirred at that temperature for 30 minutes. The resulting white slurry is cooled to about −70° C. and 20.98 mmoles of the Grignard reagent prepared from 2-bromo-6-methoxynaphthalene in tetrahydrofuran are added over a one hour period. The mixture is stirred for four hours at −70° C. and then allowed to warm to −20° C. Then it is poured into 150 ml. of dilute hydrochloric acid and extracted with methylene chloride. The organic extracts are evaporated to dryness and the remaining material is extracted with ethyl ether. The resulting slurry is filtered, to afford (S) 1-(6-methoxy-2-naphthyl)-2-methanesulfonyloxypropan-1-one, exhibiting a melting point of about 150°–154° C.

EXAMPLE 39

A mixture of 47.2 mmoles of lithium chloride and 21.3 mmoles of manganese chloride in 50 ml. of anhydrous tetrahydrofuran is stirred at 25° C. until a yellow solution is formed. Then the Grignard prepared from 19.8 mmoles of 6-methoxy-2-bromonaphthalene in tetrahydrofuran is added at −30° C. That mixture is stirred at −30° C. for 1.5 hours and then at 25° C. for 20 minutes. The solution of (6-methoxy-2-naphthyl)manganese chloride is added to 22.3 mmoles of (S) 2-methanesulfonyloxypropionyl chloride in 30 ml. of tetrahydrofuran material at −20° C. The mixture is stirred for 1 hour at −20° C., then allowed to warm to 25° C., at which temperature it is stirred for an additional hour. After that time, the mixture is poured into 150 ml. of dilute aqueous hydrochloric acid and extracted with methylene chloride. The methylene chloride is removed by evaporation under reduced pressure and ethyl ether is added. The ethereal slurry is filtered to afford (S) 1-(6-methoxy-2-naphthyl)-2-methanesulfonyloxypropan-1-one, melting at about 148°–150° C.

EXAMPLE 40

A dry flask is charged with 80.6 mmoles of imidazole and 50 ml. of anhydrous tetrahydrofuran. Then a solution of 40.3 mmoles of (S) 2-methanesulfonyloxypropionyl chloride in 50 ml. of tetrahydrofuran is added dropwise at room temperature. A white precipitate begins to form during the addition period. The mixture is allowed to stir at room temperature for 2.5 hours, and the resulting white slurry is filtered to remove the imidazole hydrochloride salt. The filtrate, containing 1-(2-methanesulfonyloxypropionyl)imidazole, is cooled to −10° C. under nitrogen and 40.0 mmoles of the magnesium Grignard of 2-bromo-6-methoxynaphthalene in tetrahydrofuran is added dropwise at −70° C. to −60° C. The mixture is stirred for 40 minutes, allowed to warm to 10° C. and poured into 150 ml. of dilute hydrochloric acid. That mixture is extracted with methylene chloride and the organic extracts are evaporated to dryness. The solid is washed with ethyl ether and dried to afford (S) 1-(6-methoxy-2-naphthyl)-2-methanesulfonyloxypropan-1-one, exhibiting an $[\alpha]_{25}^D = -29.2°$ in methylene chloride.

EXAMPLE 41

An appropriately sized dry vessel is charged with 20 grams of magnesium shavings and 15 ml. of anhydrous tetrahydrofuran. The stirred mixture is warmed to 50°–60° C. and treated with a solution of 16.6 grams of 2-bromo-6-methoxynaphthalene in 35 ml. of anhydrous tetrahydrofuran. Then the mixture is stirred for one hour at 50°–60° C. The Grignard solution is transferred to another dry vessel and cooled to 25°. 4.8 Grams of powdered zinc chloride is added to the stirred Grignard solution and the temperature of the mixture is allowed to rise to 45°–50° C. to afford a solution containing di(6-methoxy-2-naphthyl)zinc.

EXAMPLE 42

A solution of 15.7 grams of (S) 2-methanesulfonyloxypropionyl chloride in 94 ml. of dry tetrahydrofuran is cooled, with stirring, to −60° C. Then the solution of di(6-methoxy-2-naphthyl)zinc prepared in Example 42 is added over a four hour period. After the addition is completed, the reaction mixture is allowed to warm to 25° C. over a 15 hour period. The resulting mixture is added to a stirred mixture containing 30 ml. of concentrated hydrochloric acid and 200 ml. of water. 50 Ml. of diethyl ether is added and the resulting slurry is filtered and dried under reduced pressure at 40° C. to yield (S) 1-(6-methoxy-2-naphthyl)-2-methanesulfonyloxypropan-1-one.

EXAMPLE 43

A mixture of 3.07 grams of (S) 1,1-dimethoxy-1-(6-methoxy-2-naphthyl)prop-2-yl methanesulfonate, 1.0 gram of calcium carbonate, 100 ml. of dimethylformamide and 25 ml. of water is heated to 110° C. and maintained at that temperature for 5 hours. Then the mixture is cooled and the insolubles removed by filtration. The filtrate is poured into excess water and the solid which forms is collected by filtration. Separation by chromatography yields methyl 2-(6-methoxy-2-naphthyl)propionate, exhibiting an $[\alpha]_{25}{}^D = +77°$ in chloroform and an optical purity of greater than 99 percent.

While this invention has been described in reference to specific embodiments thereof, it should be understood by those skilled in the art that various changes can be made and equivalents may be substituted without departing from the true spirit and scope of the invention. All such modifications are intended to be within the scope of the claims appended hereto.

What is claimed is:

1. A process for producing a stereoisomer of the compound of the formula:

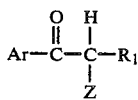

in the substantial absence of any other stereoisomer of said compound which comprises contacting an organometallic compound of the formula:

ArMX with an optically active acyl halide, acyl amine or acid anhydride of the formula:

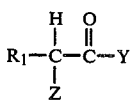

wherein Ar is substituted or unsubstituted naphthyl, M is magnesium, $R_1$ is methyl, X is halogen, Y is halogen, the group of the formula:

wherein R' and R'' are alkyl or aryl or when taken together with N form a heterocyclic moiety which optionally can contain other hetero atoms, or acyloxy, and Z is a protected hydroxy group or a sulfonyloxy group of the formula:

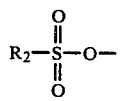

wherein $R_2$ is alkyl, cycloalkyl, alkenyl, alkynyl, aryl or arylalkyl.

2. A process for producing a material consisting essentially of a single stereoisomer of a compound of the formula:

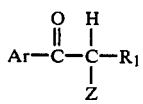

which comprises contacting an organometallic compound of the formula:

ArMX with a material consisting essentially of a single stereoisomer of an acyl halide, acyl amine or acid anhydride of the formula:

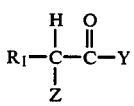

wherein Ar is substituted or unsubstituted naphthyl, M is magnesium, $R_1$ is methyl, X is halogen, Y is halogen, the group of the formula:

wherein R' and R'' are alkyl or aryl or when taken together with N form a heterocyclic moiety which optionally can contain other hetero atoms, or acyloxy, and Z is a protected hydroxy group or a sulfonyloxy group of the formula:

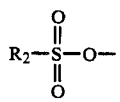

wherein $R_2$ is alkyl, cycloalkyl, alkenyl, alkynyl, aryl or arylalkyl.

3. The process of claims 1, or 2 wherein Ar is 6-methoxy-2-naphthyl.

4. The process of claim 3 wherein Z is acetoxy, benzoyloxy, dihydropyranyloxy, trialkylsiloxy or a group of the formula:

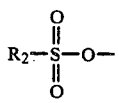

wherein $R_2$ is alkyl, cycloalkyl, alkenyl, alkynyl, aryl or arylalkyl.

5. The process of claim 4 wherein Z is alkylsulfonyloxy.
6. The process of claim 4 wherein Z is methanesulfonyloxy.
7. The process of claim 4 wherein Z is arylsulfonyloxy.
8. The process of claim 4 wherein Z is benzenesulfonyloxy.
9. The process of claim 4 wherein Z is aralkylsulfonyloxy.
10. The process of claim 4 wherein Z is p-toluenesulfonyloxy.
11. A process for producing an α-arylalkanoic acid of the formula:

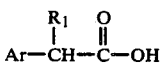

which comprises:
contacting an organometallic compound of the formula:

$$ArMX, (Ar)_2M \text{ or } ArM'$$

with an acyl halide, an acyl amine or an acid anhydride of the formula:

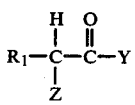

wherein Ar is aryl, M is cadmium, copper(II), manganese, magnesium or zinc, M' is copper(I) or lithium, $R_1$ is alkyl or cycloalkyl, X is halogen, Y is halogen, the group of the formula:

wherein R' and R" are alkyl or aryl or when taken together with N form a heterocyclic moiety which optionally can contain other hetero atoms, or acyloxy, and Z is a protected hydroxy group or a sulfonyloxy group of the formula:

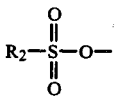

wherein $R^2$ is alkyl, cycloalkyl, alkenyl, alkynyl, aryl or arylalkyl to form a ketone of the formula:

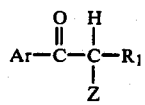

reducing said ketone to the corresponding alcohol;
contacting said alcohol so formed with a protic or dipolar, aprotic solvent for a time sufficient to form the aldehyde of the formula:

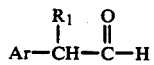

oxidizing said aldehyde to said acid, and
if Z is a protected hydroxy group, converting said group to said sulfonyloxy group either before or after said reducing step but before said contacting step.

12. The process of claim 11 wherein said acyl halide, acyl amine or acid anhydride is optically active.
13. The process of claim 12 wherein Z is a group of the formula:

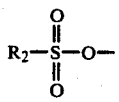

wherein $R_2$ is alkyl, cycloalkyl, alkenyl, alkynyl, aryl or aralkyl.

14. The process of claim 13 wherein Z is alkylsulfonyloxy.
15. The process of claim 13 wherein Z is methanesulfonyloxy.
16. The process of claim 13 wherein Z is arylsulfonyloxy.
17. The process of claim 13 wherein Z is benzenesulfonyloxy.
18. The process of claim 13 wherein Z is aralkylsulfonyloxy.
19. The process of claim 13 wherein Z is p-toluenesulfonyloxy.
20. The process of claims 11, 12, 13, 14, 15, 16, 17, 18 or 19 wherein said organometallic compound is ArMX in which M is magnesium and Ar is 6-methoxy-2-naphthyl, and $R_1$ is methyl.
21. The process of claim 20 wherein said ketone is reduced with a borohydride reducing agent.
22. The process of claim 21 wherein said borohydride reducing agent is sodium borohydride.
23. The process of claim 20 wherein the rearrangement of said alcohol is effected in the presence of a protic or dipolar, aprotic solvent.
24. The process of claims 20 wherein said ketone is reduced with a borohydride reducing agent and said rearrangement is effected in the presence of a protic or dipolar, aprotic solvent.

* * * * *